(12) United States Patent
Baek et al.

(10) Patent No.: US 10,123,735 B2
(45) Date of Patent: Nov. 13, 2018

(54) ELECTRONIC DEVICE FOR DETERMINING SLEEP STATE AND METHOD OF CONTROLLING SAME

(71) Applicants: Samsung Electronics Co., Ltd., Suwon-si (KR); Seoul National University R&DB Foundation, Seoul (KR)

(72) Inventors: Hyun-Jae Baek, Seoul (KR); Kwang-Suk Park, Seoul (KR); Sang-Bae Park, Cheongju-si (KR); Do-Yoon Kim, Seongnam-si (KR); Jung-Taek Oh, Seoul (KR); Jae-Geol Cho, Yongin-si (KR); Byung-Hun Choi, Suwon-si (KR); Sang-Won Seo, Seoul (KR); Hee-Nam Yoon, Yongin-si (KR); Da-Woon Jung, Yongin-si (KR); Sang-Ho Choi, Anyang-si (KR); Su-Hwan Hwang, Seoul (KR)

(73) Assignees: Samsung Electronics Co., Ltd. (KR); Seoul National University R&DB Foundation (KR)

(*) Notice: Subject to any disclaimer, the term of this patent is extended or adjusted under 35 U.S.C. 154(b) by 367 days.

(21) Appl. No.: 14/960,128

(22) Filed: Dec. 4, 2015

(65) Prior Publication Data
US 2016/0157773 A1    Jun. 9, 2016

(30) Foreign Application Priority Data
Dec. 4, 2014    (KR) .................. 10-2014-0173136

(51) Int. Cl.
*A61B 5/00*    (2006.01)
*A61B 5/053*    (2006.01)

(52) U.S. Cl.
CPC .......... *A61B 5/4809* (2013.01); *A61B 5/0533* (2013.01); *A61B 5/725* (2013.01); *A61B 5/7271* (2013.01)

(58) Field of Classification Search
CPC ... A61B 5/0531; A61B 5/0533; A61B 5/4806; A61B 5/4809; A61B 5/7271
See application file for complete search history.

(56) References Cited

U.S. PATENT DOCUMENTS

| | | | | |
|---|---|---|---|---|
| 7,774,052 B2* | 8/2010 | Burton | ............ | A61B 5/0476 600/544 |
| 8,548,770 B2* | 10/2013 | Yuen | ............ | A61B 5/0002 702/160 |

(Continued)

FOREIGN PATENT DOCUMENTS

| | | |
|---|---|---|
| JP | 2012055464 | 3/2012 |
| KR | 100646868 | 11/2006 |

(Continued)

*Primary Examiner* — Max Hindenburg
(74) *Attorney, Agent, or Firm* — McAndrews, Held & Malloy, Ltd.

(57) ABSTRACT

Disclosed is a method for an electronic device. The method may include: acquiring a galvanic skin response; generating a first parameter for a first interval and a second parameter for a second interval based on the galvanic skin response, the second interval being an interval before the first interval; determining a first threshold corresponding to the first interval based on the second parameter; and determining an activity state of the first interval based on the first threshold and the first parameter corresponding to the first interval.

18 Claims, 22 Drawing Sheets

(56) References Cited

U.S. PATENT DOCUMENTS

| | | | |
|---|---|---|---|
| 9,072,870 B2* | 7/2015 | Wu ..................... A61B 5/0031 |
| 9,498,627 B2* | 11/2016 | Rosenberg ......... A61N 1/36139 |
| 9,597,014 B2* | 3/2017 | Venkatraman ........ A61B 5/1112 |
| 9,704,209 B2* | 7/2017 | Proud .................... G06Q 50/24 |
| 9,833,196 B2* | 12/2017 | Sarrafzadeh .......... A61B 5/1118 |
| 2006/0142968 A1 | 6/2006 | Han et al. |
| 2008/0009685 A1 | 1/2008 | Kim et al. |
| 2014/0088378 A1 | 3/2014 | Muzet |

FOREIGN PATENT DOCUMENTS

| | | |
|---|---|---|
| KR | 20070120827 | 12/2007 |
| KR | 100814072 | 3/2008 |
| KR | 20120012364 | 2/2012 |
| KR | 20140058441 | 5/2014 |

* cited by examiner

ELECTRONIC DEVICE FOR DETERMINING SLEEP STATE AND METHOD OF CONTROLLING SAME

RELATED APPLICATION(S)

This application claims priority under 35 U.S.C. § 119(a) to Korean Application Serial No. 10-2014-0173136, which was filed in the Korean Intellectual Property Office on Dec. 4, 2014, the entire content of which is hereby incorporated by reference.

BACKGROUND

The present disclosure relates to an electronic device, and more particularly to an electronic device for determining an activity state of a user wearing or carrying an electronic device and a method of controlling the same. The activity state may refer to an asleep state when a user is asleep or an awake state when the user is awake.

In general, polysomnography is required to detect a sleep interval. In order to perform the polysomnography, an apparatus capable of simultaneously measuring various biometric signals such as electroencephalogram, electrooculogram, chin electromyogram, breath, etc., is needed, and a sleep specialist or a polysomnographic technologist capable of reading and analyzing various biometric signals is needed.

For the polysomnography, a user should sleep with several types of biometric signal measurement sensors attached to the body or face. However, this may cause the user to act unnaturally and thus obstruct sound sleep. Furthermore, since the user sleeps in a hospital environment, the user may have different sleep pattern than the normal sleep that occurs in a home environment.

SUMMARY

As described above, the conventional polysomnography processes are complicated and cannot be performed in a user's usual environment.

Various embodiments of the present disclosure may provide a communication method and apparatus to solve the above described problems or other problems.

In accordance with an aspect of the present disclosure, a method for an electronic device is provided. The control method includes: acquiring a galvanic skin response; generating a first parameter for a first interval and a second parameter for a second interval based on the galvanic skin response, the second interval being an interval before the first interval; determining a first threshold corresponding to the first interval based on the second parameter; and determining an activity state of the first interval based on the first threshold and the first parameter corresponding to the first interval.

In accordance with another aspect of the present disclosure, an electronic device is provided. The electronic device includes: a sensor module that acquires a galvanic skin response; and a processor that generates a first parameter for a first interval and a second parameter for a second interval based on the galvanic skin response, determines a first threshold corresponding to the first interval based on the second parameter, and determines an activity state of the first interval based on the first threshold and the first parameter corresponding to the first interval, wherein the second interval is an interval before the first interval.

In accordance with another aspect of the present disclosure, a control method of an electronic device is provided. The control method includes: acquiring a galvanic skin response; generating a first parameter for a first interval, a second parameter for a second interval, and a third parameter for a third interval based on the galvanic skin response, the second interval and the third interval being intervals before the first interval; determining an asleep state determination threshold corresponding to the first interval based on the second parameter and determining an awake state determination threshold corresponding to the first interval based on the third parameter; and determining a sleep state of the first interval based on the asleep state determination threshold and determining an awake state of the first interval based on the awake state determination threshold.

In accordance with another aspect of the present disclosure, an electronic device is provided. The electronic device includes: a sensor module that acquires a galvanic skin response; and a processor that generates a first parameter for a first interval, a second parameter for a second interval, and a third parameter for a third interval based on the galvanic skin response, determines an asleep state determination threshold corresponding to the first interval based on the second parameter, determines an awake state determination threshold corresponding to the first interval based on the third parameter, determines a sleep state of the first interval based on the asleep state determination threshold, and determines an awake state of the first interval based on the awake state determination threshold, wherein the second interval and the third interval are intervals before the first interval.

In accordance with another aspect of the present disclosure, a control method of an electronic device is provided. The control method includes: acquiring motion information on the electronic device; generating a first parameter for a first interval and a second parameter for a second interval based on the motion information, the second interval being an interval before the first interval; determining a first threshold corresponding to the first interval based on the second parameter; and determining a sleep state of the first interval based on the first threshold and the first parameter corresponding to the first interval.

In accordance with another aspect of the present disclosure, an electronic device is provided. The electronic device includes: a sensor module that acquires motion information on the electronic device; and a processor that generates a first parameter for a first interval and a second parameter for a second interval based on the motion information, determines a first threshold corresponding to the first interval based on the second parameter, and determines a sleep state of the first interval based on the first threshold and the first parameter corresponding to the first interval, wherein the second interval is an interval before the first interval.

In accordance with another aspect of the present disclosure, a control method of an electronic device is provided. The control method includes: acquiring motion information on the electronic device; generating a first parameter for a first interval, a second parameter for a second interval, and a third parameter for a third interval based on the motion information, the second interval and the third interval being intervals before the first interval; determining an asleep state determination threshold corresponding to the first interval based on the second parameter and determining an awake state determination threshold corresponding to the first interval based on the third parameter; and determining a sleep state of the first interval based on the asleep state determination threshold and determining an awake state of the first interval based on the awake state determination threshold.

In accordance with another aspect of the present disclosure, an electronic device is provided. The electronic device includes: a sensor module that acquires motion information on the electronic device; and a processor that generates a first parameter for a first interval, a second parameter for a second interval, and a third parameter for a third interval based on the motion information, determines an asleep state determination threshold corresponding to the first interval based on the second parameter, determines an awake state determination threshold corresponding to the first interval based on the third parameter, determines an asleep state of the first interval based on the asleep state determination threshold, determines an awake state of the first interval based on the awake state determination threshold, wherein the second interval and the third interval are intervals before the first interval.

In accordance with another aspect of the present disclosure, a control method of an electronic device is provided. The control method includes: acquiring at least one of a galvanic skin response and motion information on the electronic device; and determining and displaying one of an asleep state and an awake state corresponding to a current interval based on the acquired galvanic skin response.

In accordance with another aspect of the present disclosure, an electronic device is provided. The electronic device includes: a sensor module that acquires at least one of a galvanic skin response and motion information on the electronic device; and a processor that determines and displays one of an asleep state and an awake state corresponding to a current interval based on the acquired galvanic skin response.

In accordance with another aspect of the present disclosure, a control method of an electronic device is provided. The control method includes: acquiring at least one of a galvanic skin response and motion information on the electronic device; determining one of an asleep state and an awake state corresponding to a current interval based on the acquired galvanic skin response; determining one of an asleep state and an awake state corresponding to a current interval based on the motion information; and determining sleep information on the current interval based on the state of the current interval determined based on the galvanic skin response and the state of the current interval determined based on the motion information.

In accordance with another aspect of the present disclosure, an electronic device is provided. The electronic device includes: a sensing module that acquires at least one of a galvanic skin response and motion information on the electronic device; and a processor that determines one of an asleep state and an awake state corresponding to a current interval based on the acquired galvanic skin response, determines one of an asleep state and an awake state corresponding to a current interval based on the motion information, and determines sleep information on the current interval based on the state of the current interval determined based on the galvanic skin response and the state of the current interval determined based on the motion information.

According to various embodiments of the present disclosure, an electronic device capable of determining an asleep state or an awake state of a current interval and a control method of an electronic device can be provided.

Accordingly, through the analysis of a sleep interval based on a biological signal extracted from a single signal source, the power consumption of a system can be minimized, the system can be made portable, and an algorithm can be conveniently used. Furthermore, a signal can be measured without a second party's assistance.

The electronic device can be simply manufactured as a watch type equipment and directions thereof are relatively simple, so that the electronic device can be applied to general users in a normal home environment.

Furthermore, since signal measurement is not obtrusive, sleep disruption can be minimized.

Moreover, it is possible to minimize the efforts of an analyzer through an automatic algorithm for estimating the sleep interval and to also minimize the costs of inspection.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION

Figure 1:
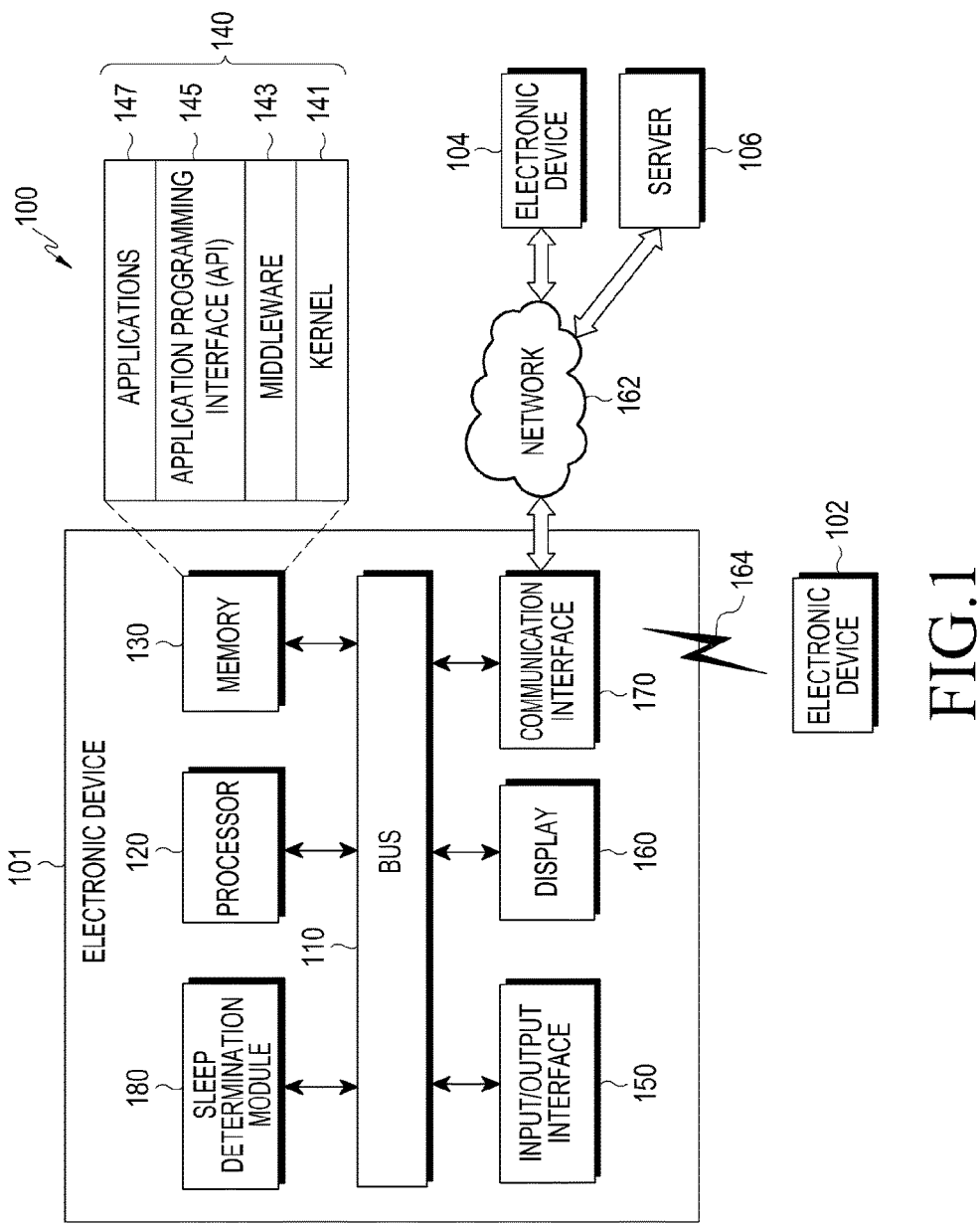
FIG. 1 illustrates a network environment including an electronic device according to various embodiments of the present disclosure.

Hereinafter, the present disclosure will be disclosed with reference to the accompanying drawings. Since various changes may be made to the present disclosure and the present disclosure may have several embodiments, particular embodiments are illustrated in the drawings and a related detailed description will be provided. However, the present disclosure is not intended to limit the present disclosure to particular embodiments, and it should be construed as including various modifications, equivalents, and/or alternatives according to the embodiments of the present disclosure. In regard to the description of the drawings, like reference numerals refer to like elements.

An expression such as "comprising" or "may comprise" may be used in the present disclosure to indicate existence of a corresponding function, operation, or component and does not exclude existence of additional functions, operations, or components. In the present disclosure, the term "comprising" or "having" indicates a characteristic, a number, a step, a component, a part, a part, or a combination thereof, and should not be construed as excluding existence or a possibility of addition of one or more other characteristics, numbers, steps, operations, components, parts, or combinations thereof.

In the present disclosure, an expression such as "A and/or B" may include all possible combinations of together listed items. For example, "A and/or B" may indicate (1) including at least one A, (2) including at least one B, or (3) including at least one A and at least one B.

Expressions such as "first," "second," "primary," or "secondary," used in descriptions of various exemplary embodiments may represent various elements regardless of order and/or importance and do not necessarily indicate relative importance of or specific order of corresponding elements. The expressions may be used for distinguishing one element from another element. For example, a first user device and a second user device may represent different user devices regardless of order or importance. For example, a first element may be referred to as a second element without deviating from the scope of the present disclosure, and similarly, a second element may be referred to as a first element.

When it is described that a first element is "operatively or communicatively coupled" or "connected" to a second element, the first element can be directly connected to the second element or it can be connected to the second element through a third element. However, when it is described that a first element is "directly connected" or "directly coupled" to a second element, it means that there is no intermediate element (such as a third element) between the first element and the second element.

The expression "configured to" used in the present disclosure may be replaced with, for example, "set to," "suitable for," "having the capacity to," "designed to," "adapted to," "made to," or "capable of" according to a situation. The expression "configured to" does not necessarily mean "specifically designed to" do a function by hardware. Alternatively, in some situation, an expression "apparatus configured to" may mean that the apparatus "can" operate together with another apparatus or component. For example, the phrase "a processor configured to perform A, B, and C" may refer to a generic-purpose processor (such as a CPU or an application processor) that can perform a corresponding operation by executing at least one software program stored at a memory device or an exclusive processor (such as an embedded processor) for performing a corresponding operation.

Terms defined in the present disclosure are used for only describing a specific exemplary embodiment and may not have an intention of limiting the scope of other exemplary embodiments. When used in the present disclosure and the appended claims, a singular form may also encompass the plural form unless it is explicitly stated otherwise. All terms including technical terms and scientific terms used here may have the same meaning as generally understood by a person of common skill in the art. Terms defined in a dictionary have the same meaning as or a meaning similar to that of a context of related technology and should not be analyzed to have an ideal or excessively formal meaning unless explicitly defined as such. Terms defined in the present disclosure should not be analyzed to exclude the present exemplary embodiments.

An electronic device according to various embodiments of the present disclosure may be a device including a communication function. For example, the electronic device may include at least one of, for example, a smart phone, a tablet Personal Computer (tablet PC), a mobile phone, a video phone, an electronic book (e-book) reader, a desktop PC, a laptop PC, a netbook computer, a Personal Digital Assistant (PDA), a Portable Multimedia Player (PMP), an MP3 player, mobile medical equipment, a camera, and a wearable device (e.g., smart glasses, Head-Mounted Device (HMD), an electronic cloth, an electronic bracelet, an electronic necklace, an appcessory, an electronic tattoo, a smart mirror, or a smart watch).

According to some embodiments of the present disclosure, the electronic device may be a smart home appliance. The home appliance may include, for example, at least one of a Television (TV), a Digital Video Disk (DVD) player, audio equipment, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ or PlayStation™), an electronic dictionary, an electronic key, a camcorder, and an electronic frame.

According to another embodiment of the present disclosure, the electronic device may include at least one of various equipments such as, for example, a blood sugar measurement device, a heartbeat measurement device, a blood pressure measurement device, or a body temperature measurement device, Magnetic Resonance Angiography (MRA) device, Magnetic Resonance Imaging (MRI) device, Computed Tomography (CT) device, an imaging device, or an ultrasonic device, a navigation system, a Global Positioning System (GPS) receiver, an Event Data Recorder (EDR), a Flight Data Recorder (FDR), a vehicle infotainment device, electronic equipment for ships (e.g., navigation system and gyro compass for ships), avionics, a security device, a vehicle head unit, an industrial or home robot, an Automatic Teller Machine (ATM), a Point of Sales (POS), Internet of Things (IoT) (e.g., electric bulbs, various sensors, electricity or gas meters, sprinkler devices, fire alarm devices, thermostats, streetlights, toasters, exercise machines, hot-water tanks, heaters, boilers, etc.).

According to some embodiments of the present disclosure, the electronic device may include a part of furniture or building/structure, an electronic board, an electronic signature receiving device, a projector, and various measuring instruments (e.g., a water, electricity, gas, or electric wave measuring device). The electronic device according to various embodiments of the present disclosure may be one of the above-listed devices or a combination thereof. The electronic device according to various embodiments of the present disclosure may be a flexible device. It will be obvious to those of ordinary skill in the art that the electronic device according to various embodiments of the present disclosure is not limited to the above-listed devices and may include new electronic devices according to technical development.

Hereinafter, an electronic device according to various embodiments of the present disclosure will be described with reference to the accompanying drawings. Herein, the term "user" used in various embodiments of the present disclosure may refer to a person who uses the electronic device or a device using the electronic device (e.g., an artificial intelligence electronic device).

FIG. 1 illustrates a network environment including an electronic device according to various embodiments of the present disclosure. Referring to FIG. 1, an electronic device 101 within a network environment 100 according to various embodiments is described. The electronic device 101 may include a bus 110, a processor 120, a memory 130, an input/output (I/O) interface 150, a display 160, a communication interface 170, and a sleep determination module 180. According to some embodiments, the electronic device 101 may omit at least some of the above components and/or may include other components.

The bus 110 may include a circuit for interconnecting the processor 120, the memory 130, the I/O interface 150, the display 160, the communication interface 170, and the sleep determination module 180 to allow for communication among these components. Accordingly, the processor 120 can receive a command from other components such as, for example, the memory 130, the I/O interface 150, the display 160, the communication interface 170, and the sleep determination module 180 through the bus 110, and execute the command.

The processor 120 may include one or more of a Central Processing Unit (CPU), an Application Processor (AP), and a Communication Processor (CP). The processor 120 may control, for example, one or more other components of the electronic device 101 and/or process an operation or data related to communication. The processor 120 may be called a controller or may include a controller as a part thereof.

The memory 130 may include volatile memory and/or non-volatile memory. The memory 130 may store, for example, commands or data related to at least one other component of the electronic device 101. According to various embodiments of the disclosure, the memory 130 may store programs 140. The programs 140 may refer to software, firmware, application programs, etc. and may include a kernel 141, middleware 143, an Application Programming Interface (API) 145, and/or application programs 147. At least some of the kernel 141, the middleware 143, and the API 145 may be referred to as an Operating System (OS).

For example, the kernel 141 may control or manage system resources such as, for example, the bus 110, the processor 120, and the memory 130, which are used to execute an operation or a function implemented in the other programs (e.g., the middleware 143, the API 145, and the application programs 147). Furthermore, the kernel 141 may provide an interface through which the middleware 143, the API 145, or the application programs 147 may access individual components of the electronic device 101 to control or manage system resources.

The middleware 143 may serve as, for example, a relay to allow the API 145 or the application programs 147 to communicate with the kernel 141 to exchange data. Furthermore, in regard to task requests received from the application programs 147, the middleware 143 may perform for example, scheduling or load balancing for the task requests by using, for example, a method of assigning at least one application a priority for using the system resources (e.g., the bus 110, the processor 120, or the memory 130) of the electronic device 101.

The API 145 is an interface by which the application programs 147 control functions provided from the kernel 141 or the middleware 143, and may include, for example, at least one interface or function (e.g., instructions) for file control, window control, image processing, or text control.

In the specification, applications may be referred to as application programs.

The I/O interface 150 may deliver a command or data from a user through an input/output device (e.g., a sensor, a keyboard, or a touch screen) to the processor 120, the memory 130, the communication interface 170, or the sleep determination module 180, for example, through the bus 110. For example, the I/O interface 150 may provide data regarding a user's touch input through the touch screen to the processor 120. The I/O interface 150 may output the command or data, received from the processor 120, the memory 130, the communication interface 170, or the sleep determination module 180 through the bus 110, through an I/O device (e.g., a speaker or a display). For example, the I/O interface 150 may output voice data processed by the processor 120 to the user through a speaker.

The display 160 may include, for example, a Liquid Crystal Display (LCD), a Light Emitting Diode (LED) display, an Organic Light Emitting Diode (OLED) display, a Micro Electro Mechanical System (MEMS) display, or an electronic paper display. The display 160 may display various types of contents (e.g., text, images, videos, icons, or symbols) to users. The display 160 may include a touch screen and may receive, for example, a touch input, a gesture input, a proximity input, or a hovering input using an electronic pen or a user's body part.

The communication interface 170 may configure communication between, for example, the electronic device 101 and an external device (e.g., a first electronic device 102, a second electronic device 104, or a server 106). For example, the communication interface 170 may be connected to a network 162 through wireless or wired communication to communicate with the external device (e.g., the second electronic device 104 or the server 106).

The wireless communication protocol used may be, for example, at least one of Long Term Evolution (LTE), Long Term Evolution-Advanced (LTE-A), Code Division Multiple Access (CDMA), Wideband Code Division Multiple Access (WCDMA), Universal Mobile Telecommunication System (UMTS), Wireless Broadband (WiBro), and Global System for Mobile communication (GSM). The wired communication may include, for example, at least one of a Universal Serial Bus (USB), a High Definition Multimedia Interface (HDMI), Recommended Standard 232 (RS-232), and a Plain Old Telephone Service (POTS). The network 162 may include a telecommunications network, for example, at least one of a computer network (e.g., LAN or WAN), Internet, and a telephone network.

Each of the first electronic device 102 and second electronic device 104 may be a device that is the same type as, or a different type from, the electronic device 101. According to an embodiment, the server 106 may include a group of one or more servers. According to various embodiments, all or some of the operations performed by the electronic device 101 may be performed by another electronic device or a plurality of other electronic devices (e.g., the first electronic devices 102, the second electronic device 104 or the server 106). According to an embodiment, when the electronic device 101 should perform some functions or services automatically or by request, the electronic device 101 may request another device (e.g., the first electronic device 102, the second electronic device 104 or the server 106) to perform at least some of the functions related to the functions or services rather than performing the functions or services by itself. Other electronic device(s) (e.g., the first electronic device 102, the second electronic device 104, and/or the server 106) may carry out the requested function or the additional function and transfer the result, obtained by carrying out the function, to the electronic device 101. The electronic device 101 may provide the requested functions or services based on the received result as is or after additionally processing the received result. To achieve this, for example, cloud computing, distributed computing, or client-server computing technology may be used.

The sleep determination module 180 may process at least a part of information obtained from, for example, the processor 120, the memory 130, the I/O interface 150, the display 160, and/or the communication interface 170, and provide the obtained information to the user.

The sleep determination module 180 is illustrated as a module separated from the processor 120 in FIG. 1, but embodiments of the disclosure need not be so limited. The entire function of the sleep determination module 180 may be included in the processor 120, the memory 130, the I/O interface 150, the display 160, and/or the communication interface 170.

The sleep determination module 180 may control at least some functions of the electronic device 101 through the use of the processor 120 or independently therefrom so that the electronic device 101 may interwork with other electronic devices (e.g., the first electronic device 102, the second electronic device 104, and/or the server 106).

Figure 2:
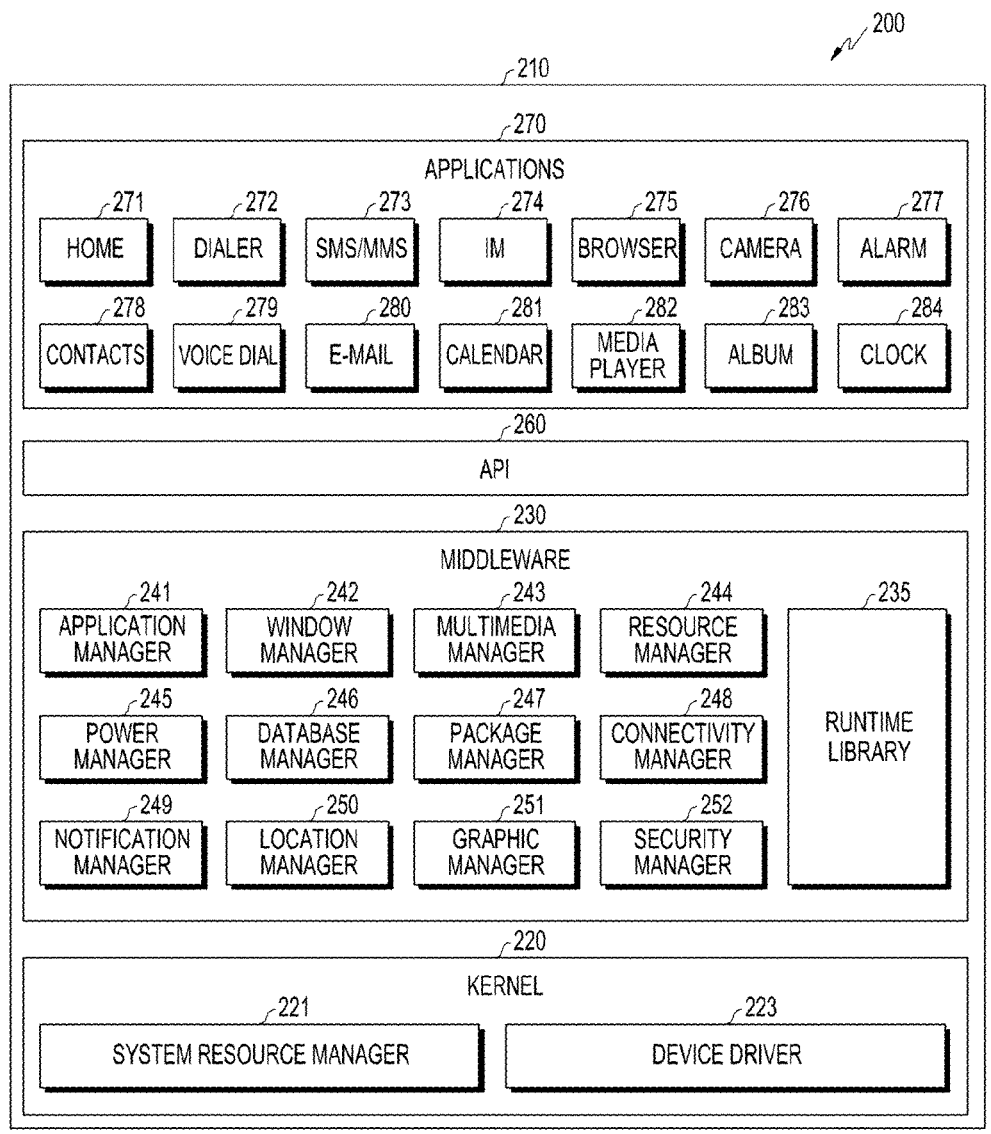
FIG. 2 is a block diagram of a program module according to various embodiments of the present disclosure.

FIG. 2 is a block diagram 200 of a program module 210 according to various embodiments of the present disclosure. Referring to FIG. 2, the program module 210 (e.g., the programs 140) may include an Operating System (OS) for controlling resources related to the electronic device (e.g., the electronic device 101) and/or various applications (e.g., the application programs 147) executed in the operating system.

The program module 210 may include a kernel 220, middleware 230, an Application Programming Interface (API) 260 and/or applications 270. At least some of the program module 210 may be preloaded in an electronic device (e.g., the electronic device 101) or downloaded from the server (e.g., the server 106).

The kernel 220 (e.g., the kernel 141 of FIG. 1) may include, for example, a system resource manager 221 and/or a device driver 223. The system resource manager 221 may control, allocate, or collect the system resources. According to an embodiment, the system resource manager 221 may include, for example, a process manager, a memory manager, and/or a file system manager. The device driver 223 may include, for example, a display driver, a camera driver, a Bluetooth driver, a shared-memory driver, a USB driver, a keypad driver, a WIFI driver, an audio driver, or an Inter-Process Communication (IPC) driver.

The middleware 230 may provide a function that is required by the applications 270 or may provide various functions to the applications 270 through the API 260 so that the applications 270 may efficiently use limited system resources of the electronic device. According to an embodiment, the middleware 230 (e.g., the middleware 143) may include, for example, at least one of a run time library 235, an application manager 241, a window manager 242, a multimedia manager 243, a resource manager 244, a power manager 245, a database manager 246, a package manager 247, a connectivity manager 248, a notification manager 249, a location manager 250, a graphic manager 251, and a security manager 252.

The run time library 235 may include, for example, a library module that a compiler uses in order to add new functions through a programming language while the applications 270 execute. The run time library 235 may perform functions related to input/output management, memory management, or an arithmetic function.

The application manager 241 may manage, for example, a life cycle of at least one of the applications 270. The window manager 242 may manage a GUI resource used in a screen. The multimedia manager 243 may detect a format required for reproducing various media files and encode or decode a media file using a codec appropriate for the corresponding format. The resource manager 244 may manage resources such as a source code, a memory or a storage space of at least one of the applications 270.

The power manager 245 may operate together with, for example, a Basic Input/Output System (BIOS), so as to manage a battery or power and may provide power information required for the operation of the electronic device. The database manager 246 may generate, search for, or change a database to be used by at least one of the applications 270. The package manager 247 may manage the installation or updating of applications distributed in the form of a package file.

The connectivity manager 248 may manage wireless connections such as Wi-Fi or Bluetooth. The notification manager 249 may display or notify an event such as a received message, an appointment, a proximity notification, etc. to a user. The location manager 250 may manage location information on an electronic device. The graphic manager 251 may manage graphic effects to be provided to a user and user interfaces related to the graphic effects. The security manager 252 may provide various security functions required for system security or user authentication. According to various embodiments of the present disclosure, when an electronic device (e.g., electronic device 101) has call capability, the middleware 230 may further include a telephony manager for managing a voice call function or a video call function of the electronic device.

The middleware 230 may include a middleware module to form a combination of various functions of the aforementioned components. The middleware 230 may provide a module specialized for each type of operating system in order to provide a differentiated function. In addition, some existing components may be dynamically removed from the middleware 230, and/or new components may be added to the middleware 230.

The API 260 (e.g., the API 145), which is a set of API programming functions, may be provided in a different configuration for each operating system. For example, some operating systems may be provided one API set for each platform, while other operating systems may be provided, two or more API sets for each platform.

The applications 270 (e.g., the application programs 147) may include one or more of a home application 271, a dialer application 272, a short message service/multimedia message service (SMS/MMS) application 273, an Instant Message (IM) application 274, a browser application 275, a camera application 276, an alarm application 277, a contact information application 278, a voice dial application 279, and e-mail application 280, a calendar application 281, a media player application 282, an album application 283, and a clock application 284. Additionally, other applications such as a health care application (e.g., an application for measuring an amount of exercise or blood sugar) and an environmental information application (e.g., an application for providing atmospheric pressure, humidity, or temperature information) may also be present.

According to an embodiment, the applications 270 may include an application that supports information exchange between the electronic device (e.g., the electronic device 101) and an external electronic device (e.g., the first electronic device 102 or the second electronic device 104). This information exchange application may include, for example, a notification relay application to transmit predetermined information to the external electronic device, or a device management application to manage the external electronic device.

The notification relay application may include a function for transferring to an external electronic device (e.g., the first electronic device 102 or the second electronic device 104) notification information generated from other applications of the electronic device 101 (e.g., an SMS/MMS application, an e-mail application, a health management application, or an environmental information application). Furthermore, the notification relay application may receive notification information from, for example, an external electronic device and provide the received notification information to a user. The device management application may manage (e.g., install, delete, or update), for example, a function for at least a part of the external electronic device (e.g., the first electronic device 102 or the second electronic device 104) communicating with the electronic device (e.g., turning on/off the external electronic device itself (or some elements thereof) or adjusting brightness (or resolution) of a display), applications executed in the external electronic device, or services provided from the external electronic device (e.g., a telephone call service or a message service).

According to various embodiments of the disclosure, the applications 270 may include an application (e.g., health management application) designated according to attributes (e.g., attributes of the electronic device such as the type of electronic device which corresponds to a mobile medical device) of the external electronic device (e.g., the first electronic device 102 or the second electronic device 104). According to various embodiments of the disclosure, the applications 270 may include an application received from the external electronic device (e.g., the server 106, the first electronic device 102 or the second electronic device 104). According to various embodiments of the disclosure, the applications 270 may include a preloaded application or a third party application that can be downloaded from the server. The names of the components of the program module 210 according to the above-described embodiments may vary depending on the type of OS.

According to various embodiments of the disclosure, at least some of the program module 210 may be implemented in software, firmware, and/or hardware. At least some of the program module 210 may be executed by a processor such as, for example, the processor 120. At least some of the program module 210 may include, for example, a module, program, routine, sets of instructions, process, etc. for performing one or more functions.

Figure 3:
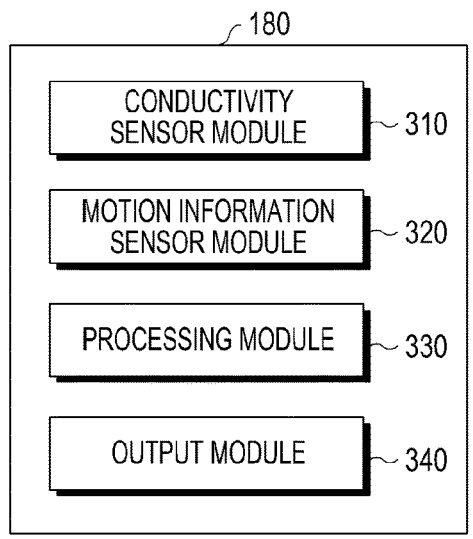
FIG. 3 is a block diagram of an asleep determination module of an electronic device according to various embodiments of the present disclosure.

FIG. 3 is a block diagram of the sleep determination module according to various embodiments of the present disclosure. Referring to FIG. 3, the sleep determination module 180 may include at least some or all of a conductivity sensor module 310, a motion information sensor module 320, a processing module 330, and an output module 340. The sleep determination module 180 may be provided separately from a processor (e.g., the processor 120) or may be entirely or partially integrated into the processor.

According to various embodiments of the present disclosure, the conductivity sensor module 310 may acquire a galvanic skin response. The processing module 330 may generate a first parameter for a first interval and a second parameter for a second interval based on the galvanic skin response, determine a first threshold corresponding to the first interval based on the second parameter, and determine an asleep state of the first interval based on the first threshold and the first parameter corresponding to the first interval. In this case, the second interval may be an interval before the first interval, where the first interval and the second interval are time intervals. Although not illustrated, the sleep determination module 180 may further include a filtering module (not shown) that low-pass filters the galvanic skin response.

The processing module 330 according to various embodiments of the present disclosure may sample the galvanic skin response in a time unit equivalent to a first period. This period of time may be referred to as a first period unit. The processing module 330 may determine a first average value of sampled data of the first interval as the first parameter and determine a second average value of sampled data of the second interval as the second parameter. As an example, the first period unit may be 3 seconds, and the first interval may be one first period unit, and the second interval may be some preset multiple of the first interval, such as, for example, N times the first interval. The preset multiple may have different values when an asleep state of the first interval is determined as opposed to when an awake state of the first interval is determined. A multiple as used in this disclosure may be any number, not necessarily just an integer.

The processing module 330 may determine threshold values to determine whether a user is in an asleep state or an awake state for a given interval of time. Depending on the value being compared to the thresholds, the processing module 330 may be unable to determine whether the user is in an asleep state or an awake state. Accordingly, the processing module may determine that the user is in an unconfirmed state for that interval. The processing module 330 may then determine an activity state of the unconfirmed interval based on activity states of intervals before and/or after the unconfirmed interval.

The output module 340 may output the activity state determined by the processing module 330 based on at least one of a visual output, a voice output, a vibration output, and signal transmission.

The processing module 330 according to various embodiments of the present disclosure may generate the first parameter for the first interval, the second parameter for the second interval, and a third parameter corresponding to a third interval based on the galvanic skin response. The processing module 330 may then determine an asleep state determination threshold corresponding to the first interval based on the second parameter, determine an awake state determination threshold corresponding to the first interval based on the third parameter, determine an asleep state of the first interval based on the asleep state determination threshold, and determine an awake state of the first interval based on the awake state determination threshold. In this case, the second interval and the third interval may be intervals before the first interval. A length of the second interval and a length of the third interval may be the same as each other or different from each other.

The processing module 330 may sample the first interval, the second interval, and the third interval to determine a first average value, a second average value, and a third average value of the sampled data as the first parameter, the second parameter, and the third parameter, respectively. The specific averaging technique may vary.

The processing module 330 may determine the average value of the second parameter of the second interval as the asleep state determination threshold and determine the average value of the third parameter of the third interval as the awake state determination threshold. When the first parameter is smaller than a preset multiple of the asleep state determination threshold, the processing module 330 may determine that the first interval corresponds to the asleep state. When the first parameter is larger than or equal to the preset multiple of the asleep state determination threshold, the processing module 330 may determine that the first interval is an unconfirmed interval. When the first parameter is larger than a preset multiple of the awake state determination threshold, the processing module 330 may determine that the first interval corresponds to the awake state. When the first parameter is equal to or smaller than the preset multiple of the awake state determination threshold, the processing module 330 may determine that the first interval is an unconfirmed interval.

The processing module 330 according to various embodiments of the present disclosure may determine sleep information on the first interval based on the sleep state of the first interval. The processing module 330 may determine an asleep state of the unconfirmed interval based on sleep states of intervals before and after the unconfirmed interval.

The motion information sensor module 320 according to various embodiments of the present disclosure may acquire motion information on the electronic device 101.

The processing module 330 according to various embodiments of the present disclosure may generate a first parameter of a first interval and a second parameter of a second interval based on the motion information, determine a first threshold corresponding to the first interval based on the second parameter, and determine an asleep state of the first interval based on the first threshold and the first parameter corresponding to the first interval. In this case, the second interval may be an interval before the first interval.

The processing module 330 according to various embodiments of the present disclosure may generate the first parameter of the first interval, the second parameter of the second interval, and a third parameter corresponding to a third interval based on the motion information, determine an asleep state determination threshold corresponding to the first interval based on the second parameter, determine an awake state determination threshold corresponding to the first interval based on the third parameter, determine an asleep state of the first interval based on the asleep state determination threshold, and determine an awake state of the first interval based on the awake state determination threshold. In this case, the second interval and the third interval may be intervals before the first interval.

The conductivity sensor module 310 and the motion information sensor module 320 according to various embodiments of the present disclosure may acquire at least one of galvanic skin response and motion information on the electronic device. The processing module 330 may determine one of asleep state and awake state corresponding to a current interval based on the acquired galvanic skin response. The output module 340 may output one of the determined asleep state and awake state.

The processing module 330 according to various embodiments of the present disclosure may determine one of asleep state and awake state corresponding to the current interval based on the galvanic skin response, determine one of asleep state and the awake state corresponding to the current interval based on the motion information, and determine sleep information on the current interval based on the state of the current interval determined based on the galvanic skin response and/or the state of the current interval determined based on the motion information.

Figure 4:
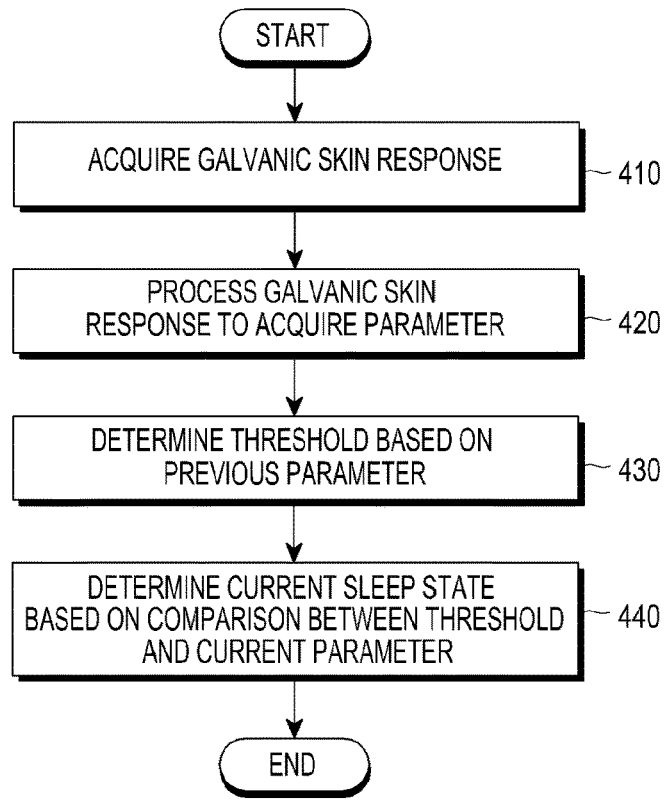
FIG. 4 is flowchart illustrating a control method of the electronic device according to various embodiments of the present disclosure.

FIG. 4 is a flowchart illustrating a control method of the electronic device according to various embodiments of the present disclosure.

In operation 410, the electronic device 101 may acquire a galvanic skin response. The galvanic skin response may be at least one of electrical resistance and potential on a human's skin. The galvanic skin response may have a waveform that varies depending on a human's excitement or a state of tension and may be a representative index indicating the activation of a human's sympathetic nervous system/parasympathetic nervous system. A human's sleep state is influenced by the activation of a human's sympathetic nervous system and parasympathetic nervous system. The parasympathetic nervous system may be activated as a human enters deeper sleep, and the sympathetic nervous system may be activated when a human awakes. A galvanic skin response signal may be classified into a skin potential signal and a skin resistance signal based on whether the galvanic skin response is a DC measurement or an AC measurement, respectively. The skin potential continuously decreases when a human falls asleep and instantaneously increases when a human awakes from sleep.

As described above, the electronic device 101 may acquire the galvanic skin response through, for example, the conductivity sensor module 310. According to an embodiment, the conductivity sensor module 310 may include an Ag/AgCl electrode. The conductivity sensor module 310 may be worn on a user's finger or the back of a user's hand and acquire a galvanic skin response from the finger or the back of user's hand.

In operation 420, the electronic device 101 may process the acquired galvanic skin response to acquire a parameter. According to an embodiment, the electronic device 101 may calculate an average value of galvanic skin responses and acquire a calculated average value as the parameter. A process of acquiring the parameter will be described in more detail with respect to FIG. 5A.

In operation 430, the electronic device 101 may determine a threshold to be used for determining an asleep state of a current interval based on a previous parameter. A process of determining the threshold will be described in more detail with respect to FIG. 5B.

In operation 440, the electronic device 101 may compare the determined threshold and the parameter of the current interval and determine the sleep state of the current interval based on a result of the comparison. A process of determining the sleep state will be described in more detail with respect to FIG. 5C.

Figure 5A:
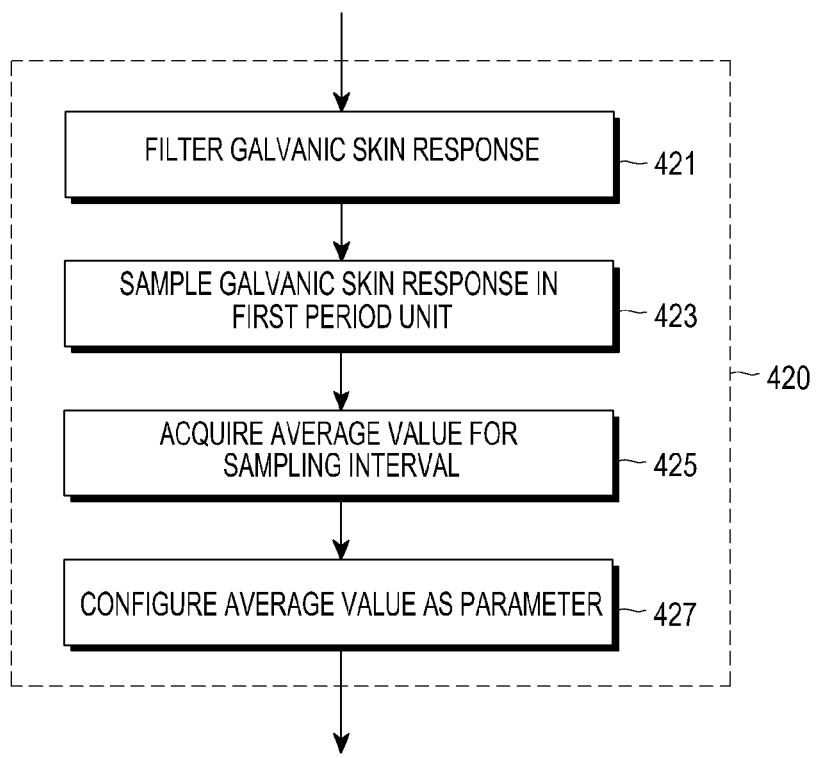
FIG. 5A is a flowchart illustrating a parameter generation process according to various embodiments of the present disclosure.
Figure 5B:
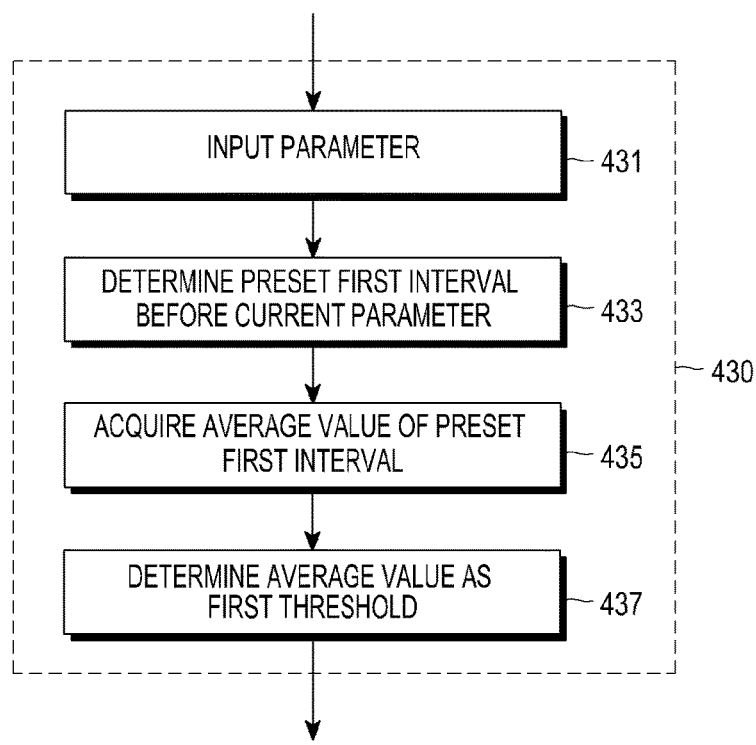
FIG. 5B is a flowchart illustrating a threshold determination process according to various embodiments of the present disclosure.
Figure 5C:
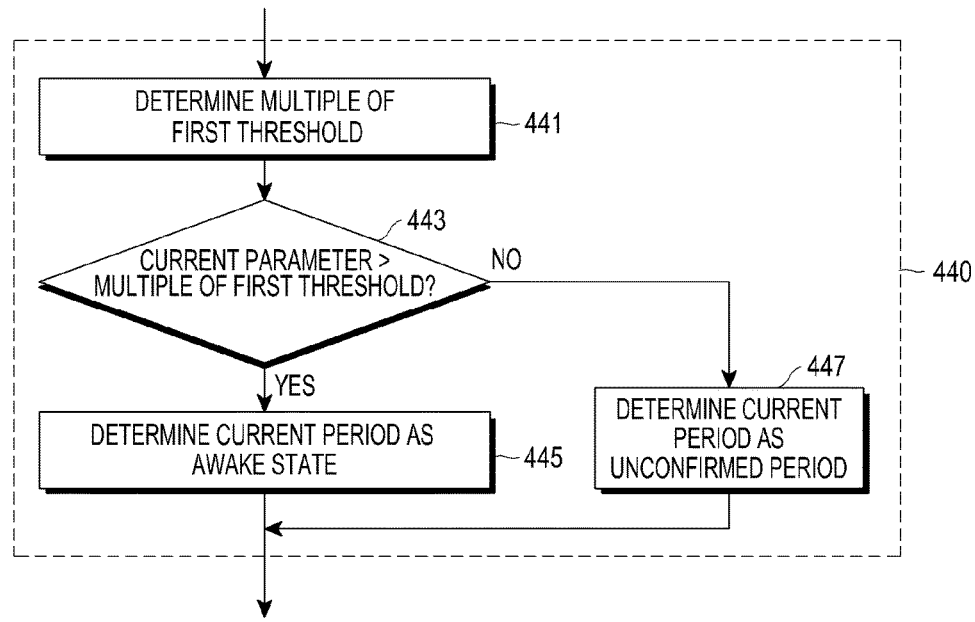
FIG. 5C is a flowchart illustrating awake state determination process according to various embodiments of the present disclosure.

FIG. 5A is a flowchart illustrating a parameter generation process according to various embodiments of the present disclosure. FIG. 5B is a flowchart illustrating a threshold determination process according to various embodiments of the present disclosure. FIG. 5C is a flowchart illustrating an asleep state determination process according to various embodiments of the present disclosure. Embodiments of FIGS. 5A to 5C will be described in more detail with reference to FIGS. 6A to 6C.

Referring first to FIG. 5A, in operation 421, the electronic device 101 may filter the galvanic skin response. According to an embodiment, the electronic device 101 may low-pass filter raw data on the galvanic skin response. The galvanic skin response may be a relatively low band signal among biometric signals, and a signal corresponding to a frequency of a preset level or higher may be noise. The electronic device 101 may amplify the low-pass filtered galvanic skin response. According to an embodiment, a low-pass filter may have a cutoff frequency of 0.5 Hz.

Figure 6A:
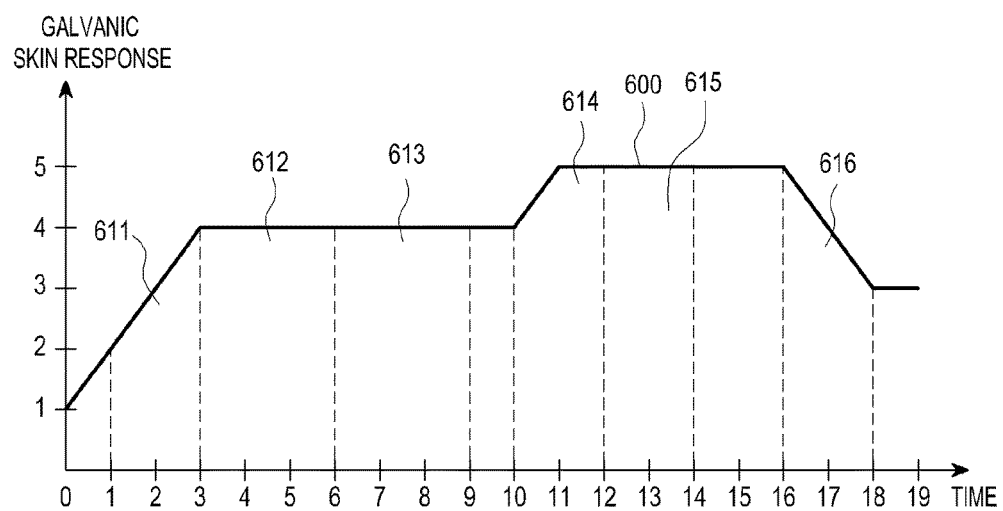
FIGS. 6A to 6C illustrate a galvanic skin response, a parameter, and a threshold according to various embodiments of the present disclosure.

FIG. 6A illustrates a galvanic skin response or a processed galvanic skin response according to various embodiments of the present disclosure. As illustrated in FIG. 6A, the electronic device 101 may measure the galvanic skin response varying between 1 V and 5 V from during a 19 second period Although it is illustrated in FIG. 6A that the electronic device 101 measures skin potential, it is only an example and the electronic device 101 may measure skin resistance.

Figure 6B:
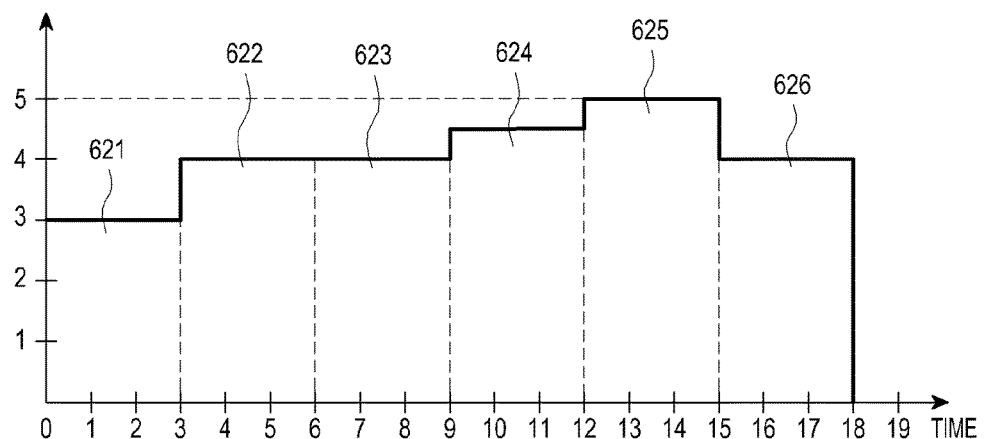

In operation 423, the electronic device 101 may sample the galvanic skin response measured in the first period unit. For example, as illustrated in FIG. 6B, the electronic device 101 may sample the galvanic skin response every 3 seconds. In operation 425, the electronic device 101 may acquire an average value of sampling intervals. For example, as illustrated in FIG. 6B, the electronic device 101 may determine an average value every 3 seconds.

In operation 427, the electronic device 101 may configure the average value as the parameter. For example, the electronic device 101 may acquire parameters shown in Table 1.

TABLE 1

| | period | | | | | |
|---|---|---|---|---|---|---|
| | First period (0 to 3) | Second period (3 to 6) | Third period (6 to 9) | Fourth period (9 to 12) | Fifth period (12 to 15) | Sixth period (15 to 18) |
| Parameter (average value) | 3 | 4 | 4 | 14/3 | 5 | 4 |

Meanwhile, although it has been described in FIG. 6B that the electronic device 101 samples the galvanic skin response in units of 3 seconds, determines the average value of sampling periods, and configures the average value as the parameter, it is only an example and there is no limitation on the sampling period. According to another embodiment, the electronic device 101 may perform the sampling in a unit of 30 seconds and, accordingly, acquire a parameter corresponding to the standard of polysomnography. In some embodiments of the present disclosure, the sampling period may be the same as the first period unit.

FIG. 5B is a flowchart illustrating the threshold determination process according to various embodiments of the present disclosure.

Figure 6C:
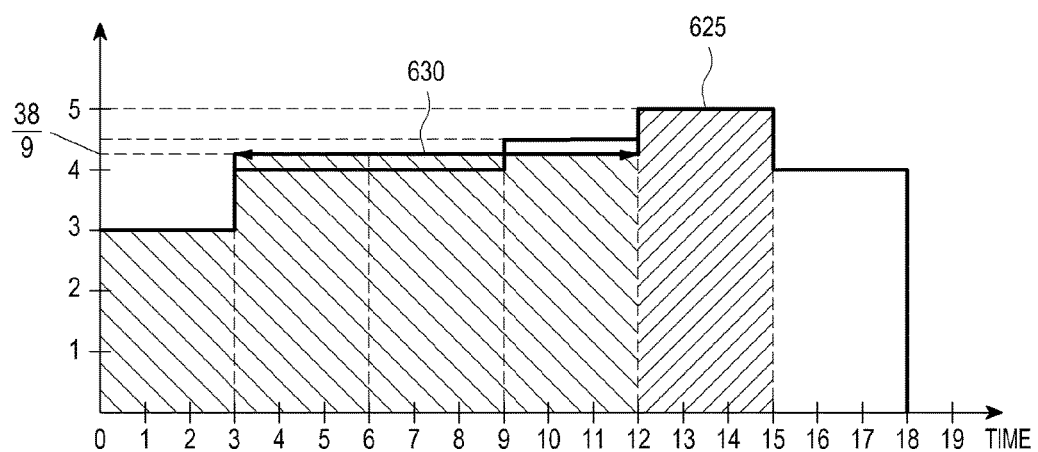

As illustrated in FIG. 5B, with reference to FIG. 6C, in operation 431, the electronic device 101 may receive a parameter. For example, the electronic device 101 may receive parameters shown in Table 1. The electronic device 101 may determine an interval 630 before the current parameter 625 as ranging from 3 seconds to 12 seconds, or 3 first period units. The interval 630 may be preset. A length of the interval 630 may be preset, for example, as a multiple of the sampling period, where the sampling period is 3 seconds in this example.

In operation 433, the electronic device 101 may determine the interval 630 before a current parameter 625. The interval 630 may vary from 3 seconds to 12 seconds, or some other period of time. For example, it is assumed that the electronic device 101 determines the sleep state (whether an awake state or an asleep state) of 12 seconds to 15 seconds in an embodiment of FIG. 6C. Accordingly, the electronic device 101 may use the current parameter 625 associated with the period from 12 seconds to 15 seconds as the current parameter.

Although it is illustrated in FIG. 6C that the electronic device 101 acquires the average value of discrete data during the interval 630 as a final value for a parameter of the interval 630, it is only an example. According to another embodiment, the electronic device 101 may acquire a final value for the parameter of the interval 630 by performing a moving average on the acquired parameters in the unit of preset samples. The electronic device 101 may successively change the discretely averaged data and, accordingly, normalize the average of the parameters.

The electronic device 101 may acquire an average value of the samples in the interval 630 in operation 435 and set the average value of the interval 630 as a first threshold in operation 437. For example, as illustrated in FIG. 6C, the electronic device 101 may determine the average value 38/9 of the interval 630 as the first threshold.

According to an embodiment of the present disclosure, the electronic device 101 may determine the average value of the interval 630 as an awake state determination threshold.

FIG. 5C is a flowchart illustrating awake state determination process according to various embodiments of the present disclosure.

In operation 441, the electronic device 101 may determine a multiplier for the first threshold. According to an embodiment, the multiplier may be 1.15. The electronic device 101 may then determine it to be 437/90, which is 1.15 times the first threshold 38/9. The value 1.15 is only an example, and it is easily understood by those skilled in the art that there is no limitation on the value.

In operation 443, the electronic device 101 may determine whether a current parameter is larger than the multiple of the first threshold. According to an embodiment, the electronic device 101 may determine that 5, which is the current parameter 625 of the current interval, is larger than 437/90 which is the multiple of the first threshold.

When the current parameter is larger than the multiple of the first threshold, the electronic device 101 may determine that the current interval corresponds to the awake state in operation 445. According to an embodiment, the electronic device 101 may determine that sleep information on the current interval of 12 seconds to 15 seconds corresponds to the awake state.

Meanwhile, when the current parameter is equal to or smaller than the multiple of the first threshold, the electronic device 101 may determine that the sleep information on the current interval of 12 seconds to 15 seconds corresponds to an unconfirmed period in operation 447.

According to another embodiment, the electronic device 101 may determine whether the user is in an awake state by determining whether the current parameter is larger than a preset constant, where this preset constant may be a preset awake state constant. Furthermore, the electronic device 101 may determine the unconfirmed period by determining whether the current parameter is equal to or smaller than a preset constant, where this preset constant may be the preset awake state constant.

It has been described above how the electronic device 101 determines the awake state. Hereinafter, a case where the electronic device 101 determines the asleep state will be described with reference to FIGS. 7 to 9. In the above description, the electronic device 101 determines an asleep state based on the threshold acquired from the parameter of the previous interval. However, according to another embodiment, the electronic device 101 may determine the current sleep state based on a comparison between the size of the parameter of the current interval and the size of the pre-stored threshold.

Figure 7:
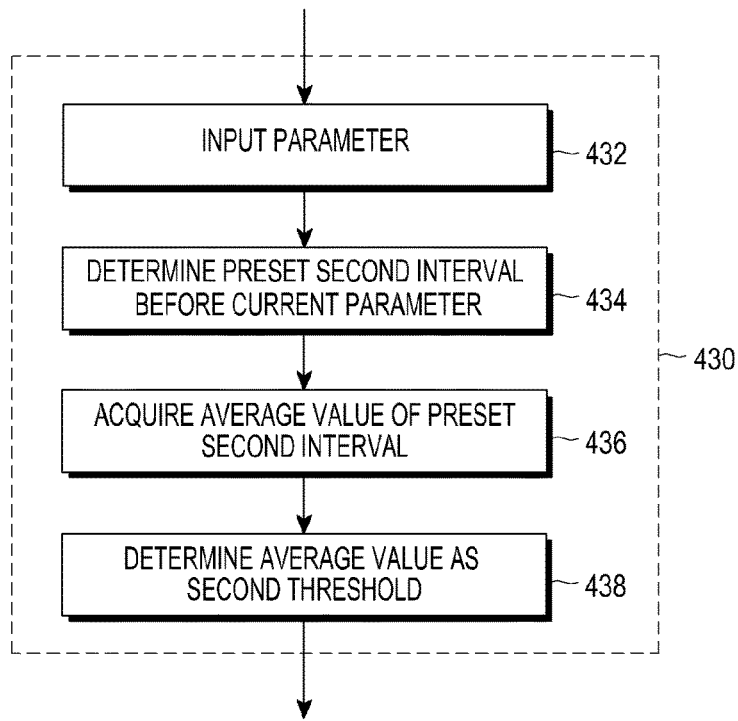
FIG. 7 is a flowchart illustrating a process of calculating an asleep state determination threshold according to various embodiments of the present disclosure.

FIG. 7 is a flowchart illustrating a process of calculating an asleep state determination threshold according to various embodiments of the present disclosure.

In operation 432, the electronic device 101 may receive a parameter. For example, the electronic device 101 may receive parameters shown in Table 1.

Figure 8:
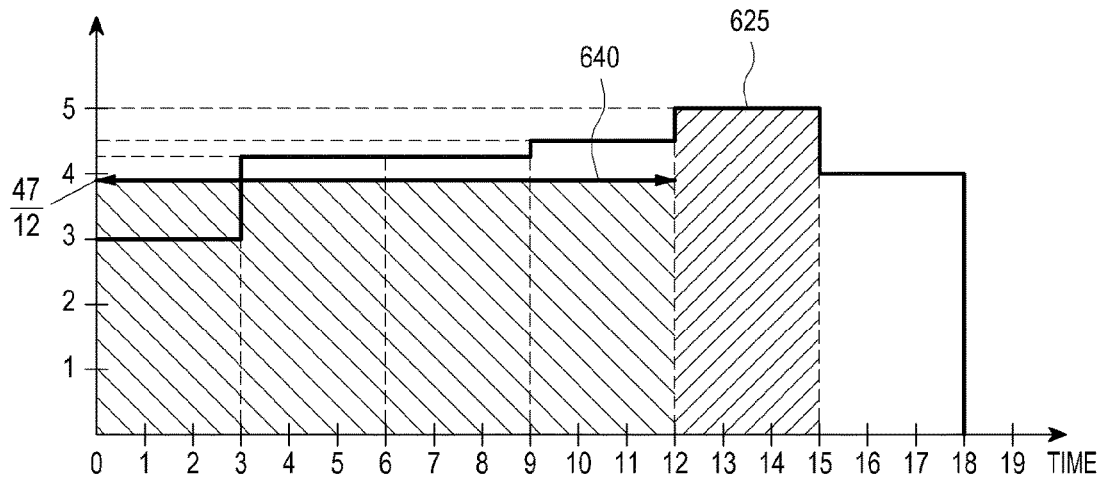
FIG. 8 illustrates an asleep state determination threshold according to various embodiments of the present disclosure.

In operation 434, the electronic device 101 may determine an interval 640 before a current parameter as illustrated in FIG. 8. The interval 640 may be preset. A length of the interval 640 may be different from the length of the interval 630 of FIG. 6C. For example, the length of the interval 630 of FIG. 6C may be 3 sampling units, and the length of the interval 640 of FIG. 8 may be the 4 sampling units. According to an embodiment, the length of the interval 640 that determines the asleep state may be larger than the length of the interval 630 that determines the awake state. According to another embodiment, the length of the interval 630 may be larger than the length of the interval 640, or the length of the interval 630 and the length of the interval 640 may be the same as each other.

The electronic device 101 may acquire an average value of the interval 640 in operation 435. In operation 437 the acquired average value determined as a second threshold that may be, for example, an asleep state determination threshold. In an embodiment of FIG. 8, the electronic device 101 may acquire the average value 47/12 of the interval 640 as the second threshold.

Figure 9:
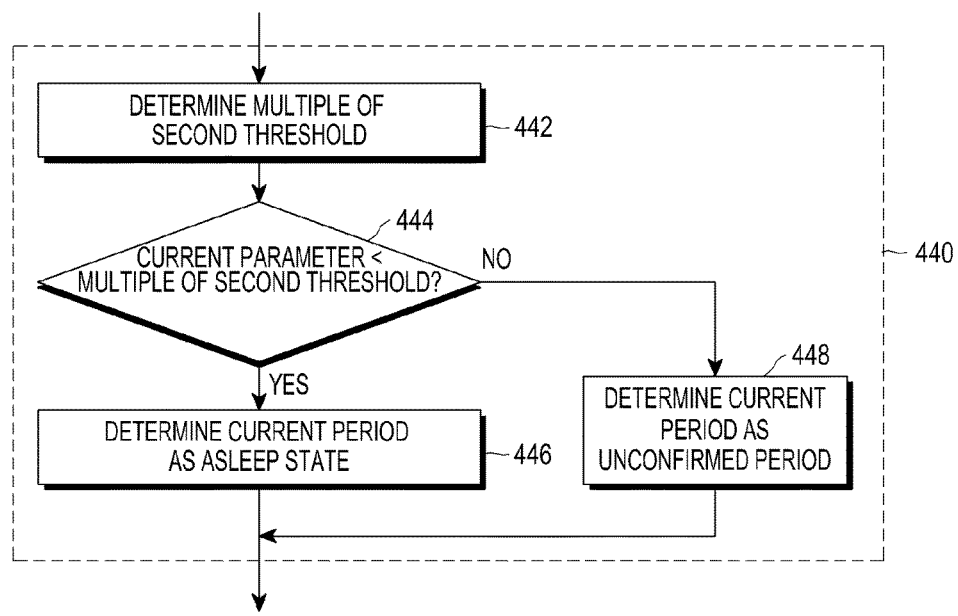
FIG. 9 is a flowchart illustrating a process of determining an asleep state according to various embodiments of the present disclosure.

FIG. 9 is a flowchart illustrating a process of determining an asleep state according to various embodiments of the present disclosure.

In operation 442, the electronic device 101 may determine a multiplier of the second threshold. According to an embodiment, the multiplier may be 1. The electronic device 101 may determine 47/12 which is 1 times the second threshold 47/12. The value 1 is only an example, and it is easily understood by those skilled in the art that there is no limitation on the value for the multiplier.

In operation 444, the electronic device 101 may determine whether a current parameter is smaller than the multiple of the second threshold. According to an embodiment, the electronic device 101 may determine that 5, which is the current parameter 625 of the current interval, is larger than 47/12, which is the multiple of the second threshold.

When the current parameter is equal to or smaller than the multiple of the second threshold, the electronic device 101 may determine that the current period corresponds to the asleep state in step 446.

In operation 448, when the current parameter is larger than or equal to the multiple of the first threshold, the electronic device 101 may determine that the sleep information for the current interval of 12 seconds to 15 seconds corresponds to an unconfirmed period. According to an embodiment, the electronic device 101 may determine that sleep information on the current interval of 12 seconds to 15 seconds corresponds to the unconfirmed period.

According to another embodiment, when the current parameter is smaller than a preset constant, the electronic device 101 may determine that the current period corresponds to the asleep state. When the current parameter is larger than or equal to the preset constant, the electronic device 101 may determine that the current period corresponds to the unconfirmed period. The preset constant may be a preset asleep state constant.

The electronic device 101 may combine results of the determination of the process of determining the awake state and the process of determining the asleep state to determine that the sleep information on the current interval of 12 seconds to 15 seconds corresponds to the awake state, which will be described below in more detail with reference to FIG. 10.

Figure 10:
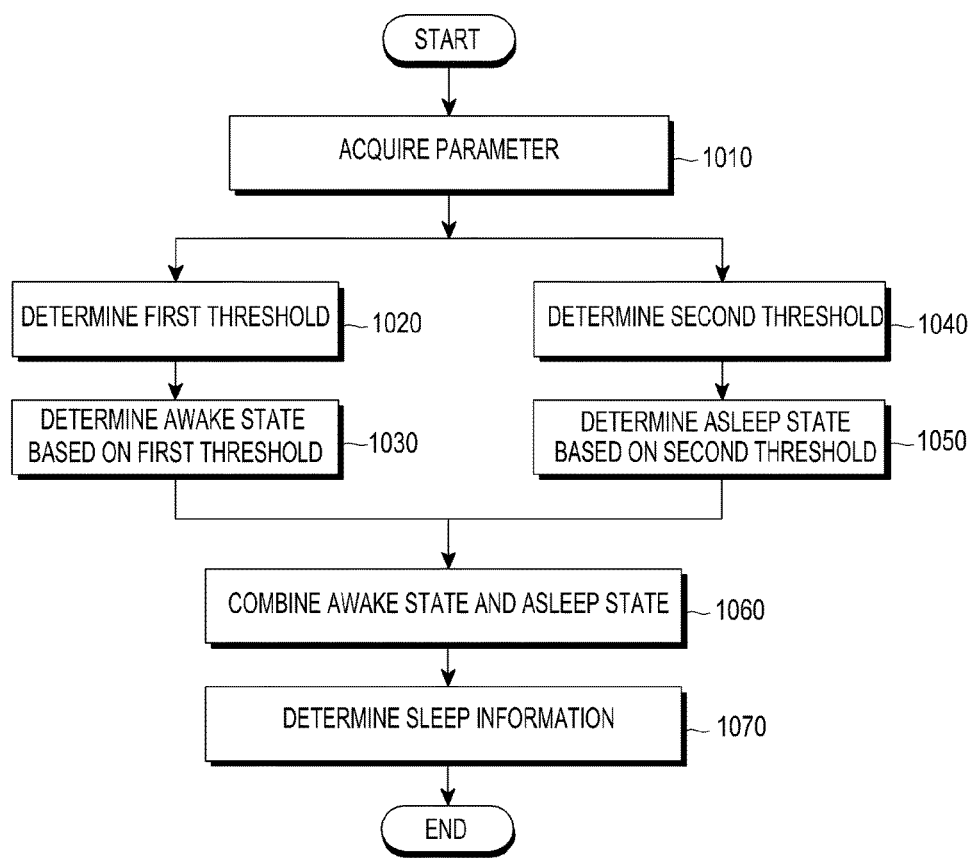
FIG. 10 is a flowchart illustrating a control method of the electronic device according to various embodiments of the present disclosure.

FIG. 10 is flowchart illustrating a control method of the electronic device according to various embodiments of the present disclosure. The embodiment of FIG. 10 will be described in more detail with reference to FIGS. 11A to 11D and FIGS. 12A to 12D. FIGS. 11A to 11D illustrate a galvanic skin response, a parameter, and a threshold, respectively, according to various embodiments of the present disclosure. FIGS. 12A to 12D illustrate an asleep state, an awake state, and sleep information, respectively, according to various embodiments of the present disclosure.

Figure 11:
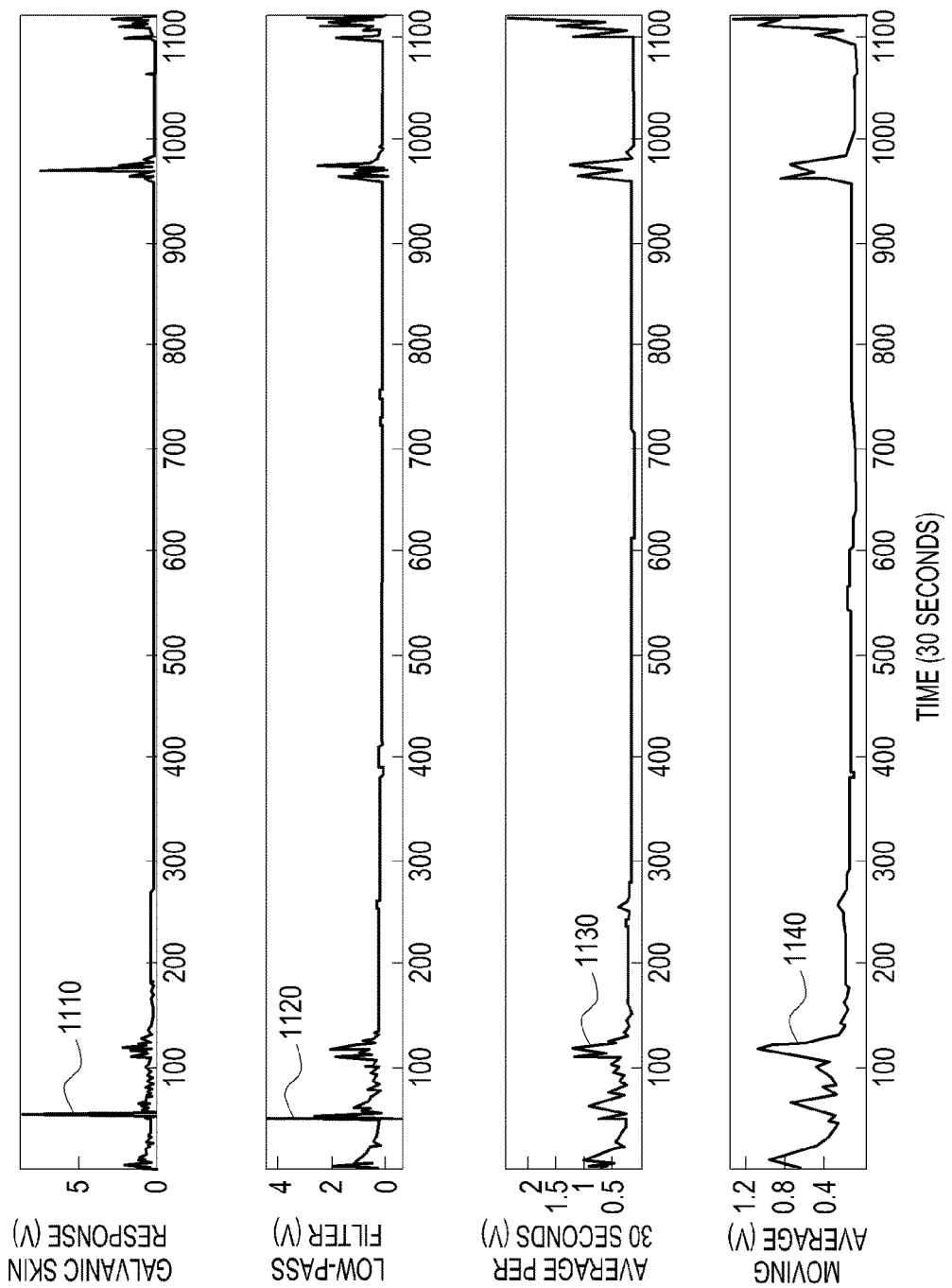
FIGS. 11A to 11D illustrate a galvanic skin response, a parameter, and a threshold according to various embodiments.

In operation 1010, the electronic device 101 may acquire a parameter. For example, the electronic device 101 may acquire a galvanic skin response 1110 as illustrated in FIG. 11A. The electronic device 101 may low-pass filter the galvanic skin response 1110 to acquire a low-pass filtered galvanic skin response 1120. The electronic device 101 may sample the low-pass filtered galvanic skin response 1120 and acquire an average value in every sampling interval to acquire a parameter 1130 as illustrated in FIG. 11C. In an embodiment of FIG. 11C, the electronic device 101 may perform the sampling in the unit of 30 seconds.

In operation 1020, the electronic device 101 may determine a first threshold corresponding to the awake state determination threshold for determining the sleep state. According to an embodiment, the electronic device 101 may determine an average value of parameters of "a" sampling intervals before the current interval as the first threshold. According to an embodiment, the electronic device 101 may acquire a continuous threshold 1140 as illustrated in FIG. 11D by performing a moving average on the acquired parameter 1130. The interval of the moving average may be the "a" sampling interval.

In operation 1030, the electronic device 101 may determine whether the sleep state is an awake state based on the first threshold. According to an embodiment, when the parameter of the current interval is larger than the first threshold, the electronic device 101 may determine the corresponding current interval as the awake state. Furthermore, when the parameter of the current interval is equal to or smaller than the first threshold, the electronic device 101 may determine the corresponding current interval as an unconfirmed period.

Figure 12:
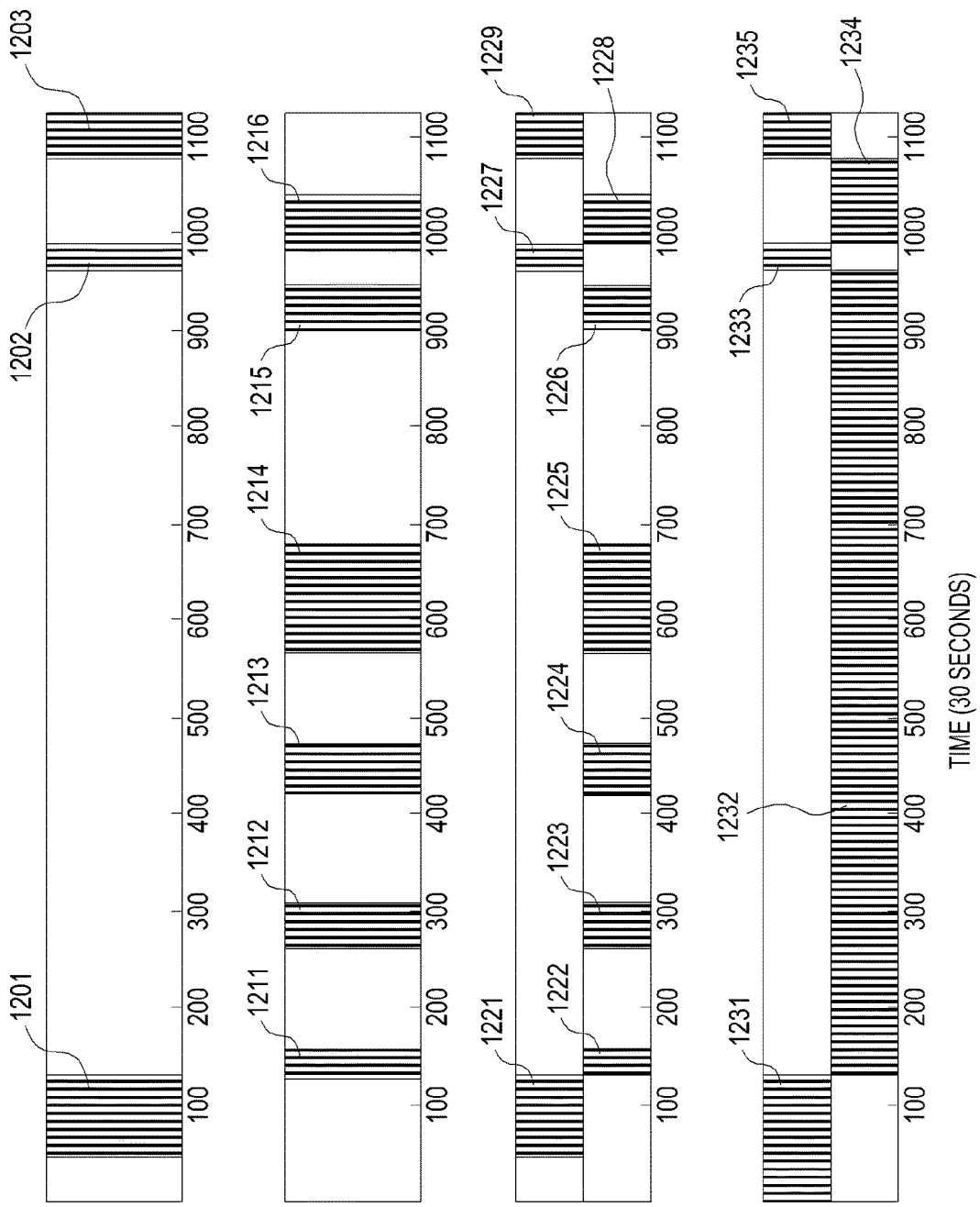
FIGS. 12A to 12D illustrate an asleep state, an awake state, and sleep information according to various embodiments of the present disclosure.

FIG. 12 illustrates the awake state according to various embodiments of the present disclosure. As illustrated in FIG. 12A, the electronic device 101 may determine intervals determined as the awake states 1201, 1202, and 1203 with respect to a sampling period. Intervals other than the awake states 1201, 1202, and 1203 may be unconfirmed periods.

In operation 1040, the electronic device 101 may determine a second threshold corresponding to the asleep state determination threshold for determining the asleep state. According to an embodiment, the electronic device 101 may determine an average value of parameters of "b" sampling intervals before the current interval as the second threshold. According to an embodiment, the electronic device 101 may perform a moving average on the acquired parameter 1130 to determine the second threshold.

In operation 1050, the electronic device 101 may determine whether the sleep state is an asleep state based on the second threshold. According to an embodiment, when the parameter of the current interval is smaller than the second threshold, the electronic device 101 may determine the corresponding current interval as the asleep state. Furthermore, when the parameter of the current interval is larger than or equal to the second threshold, the electronic device 101 may determine the corresponding current interval as an unconfirmed period.

FIG. 12B illustrates the awake state according to various embodiments of the present disclosure. As illustrated in FIG. 12B, the electronic device 101 may determine intervals determined as the asleep states 1211, 1212, 1213, 1214, 1215, and 1216 with respect to the sampling period. Intervals other than the asleep states 1211, 1212, 1213, 1214, 1215, and 1216 may be unconfirmed periods.

In operation 1060, the electronic device 101 may combine the awake state and the asleep state. For example, as illustrated in FIG. 12C, the electronic device 101 may combine the awake states 1221, 1227, and 1229 and the asleep states 1222, 1223, 1224, 1225, 1226, and 1228 in the same sampling period.

In operation 1060, the electronic device 101 may determine sleep information 1231, 1232, 1233, 1234, and 1235 based on a result of the combination. This is shown in FIG. 12D. The sleep information may include sleep information 1231, 1233, and 1235 corresponding to the awake state, and sleep information 1232 and 1234 corresponding to the asleep state. The electronic device 101 may determine an unconfirmed period between the asleep states 1222 and 1223, an unconfirmed period between the asleep states 1223 and 1224, an unconfirmed period between the asleep states 1224 and 1225, and an unconfirmed period between the asleep states 1225 and 1226 of FIG. 12C as asleep states. Based on states of periods before and after the unconfirmed period, the electronic device 101 may determine a state of the corresponding unconfirmed period. Accordingly, when the states of the periods before and after the unconfirmed period are the same as each other, the electronic device 101 may configure the state of the corresponding unconfirmed period to be the same as the states of the periods before and after the unconfirmed period.

The electronic device 101 may determine an unconfirmed period between the asleep state 1226 and the awake state 1127 and an unconfirmed period between the asleep state 1228 and the awake state 1129 as asleep states. That is, when the asleep state, the unconfirmed period, and the awake state are sequentially determined, the electronic device 101 may determine the corresponding unconfirmed period as an asleep state. The determination of the unconfirmed period as asleep state when the asleep state, the unconfirmed period, and the awake state are sequentially determined is only an example, and the electronic device 101 may instead determine the corresponding unconfirmed period as the awake state.

According to the above description, the electronic device 101 may determine sleep information on the current interval and sleep information on a predetermined interval.

Figure 13:
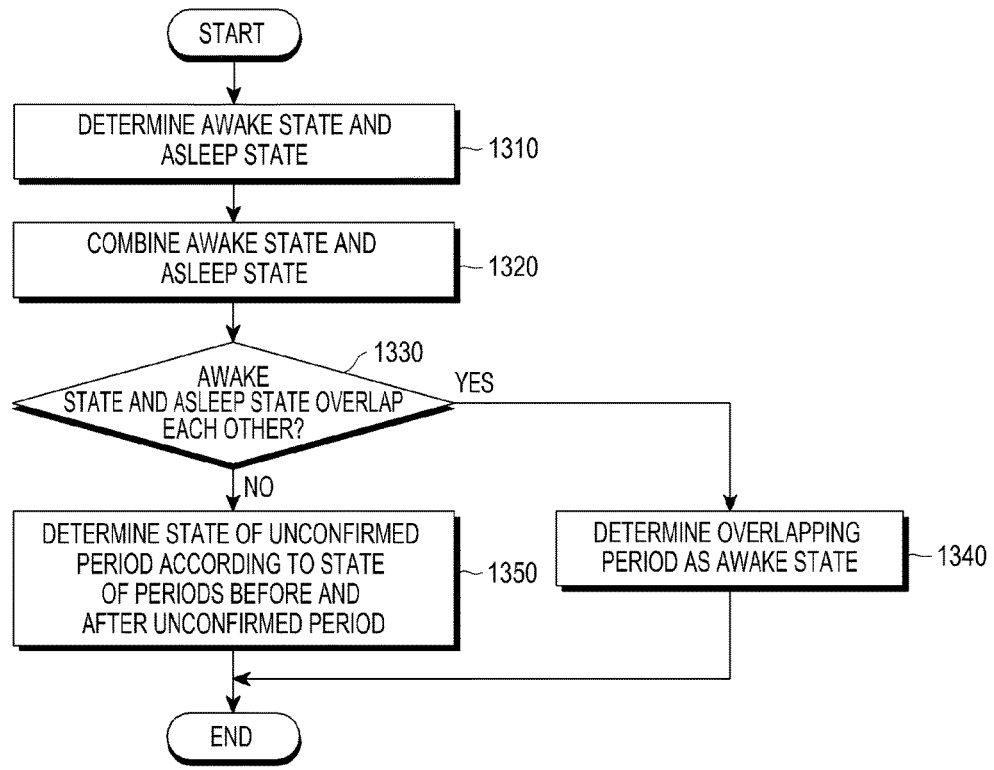
FIG. 13 is a flowchart illustrating a control method of the electronic device according to various embodiments of the present disclosure.

FIG. 13 is flowchart illustrating a control method of the electronic device according to various embodiments of the present disclosure.

In operation 1310, the electronic device 101 may determine an awake state and an asleep state. In operation 1320, the electronic device 101 may combine the awake state and the asleep state.

In operation 1330, the electronic device 101 may determine that the awake state and the asleep state overlap each other in some sampling periods based on a result of the combination of the awake state and the asleep state. In operation 1340, the electronic device 101 may determine the overlapping period as the awake state. According to another embodiment, the electronic device 101 may determine the overlapping period as the asleep state.

In operation 1350, the electronic device 101 may determine the state according to states of periods before and after the unconfirmed period with respect to the unconfirmed period.

Figure 14:
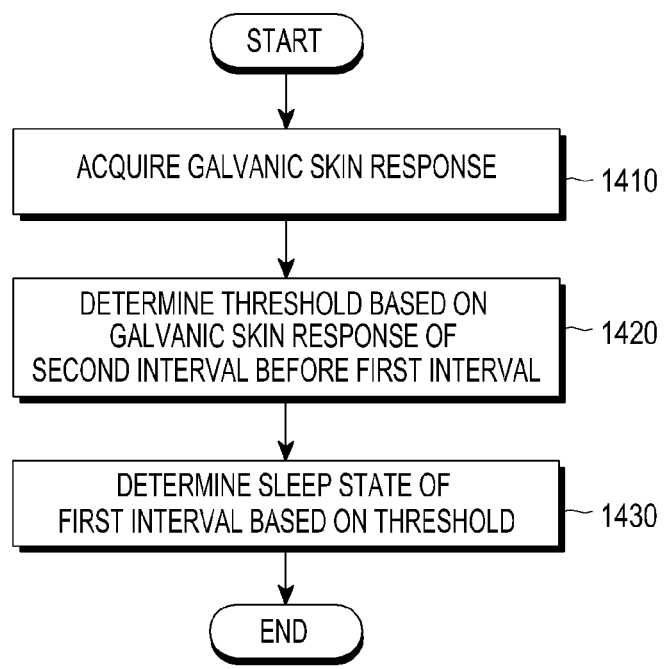
FIG. 14 is a flowchart illustrating a control method of the electronic device according to various embodiments of the present disclosure.

FIG. 14 is a flowchart illustrating a control method of the electronic device according to various embodiments of the present disclosure.

In operation 1410, the electronic device 101 may acquire a galvanic skin response.

In operation 1420, the electronic device 101 may generate a first parameter for a first interval and a second parameter for a second interval based on the galvanic skin response. The second interval may be an interval before the first interval, where the first interval and the second interval are time intervals. The electronic device 101 may determine a first threshold corresponding to the first interval based on the second parameter.

In operation 1430, the electronic device 101 may determine an asleep state of the first interval based on the first threshold and the first parameter corresponding to the first interval. According to an embodiment, the electronic device 101 may determine an asleep state based on a result of comparing a multiple of the first threshold with the first parameter.

Figure 15:
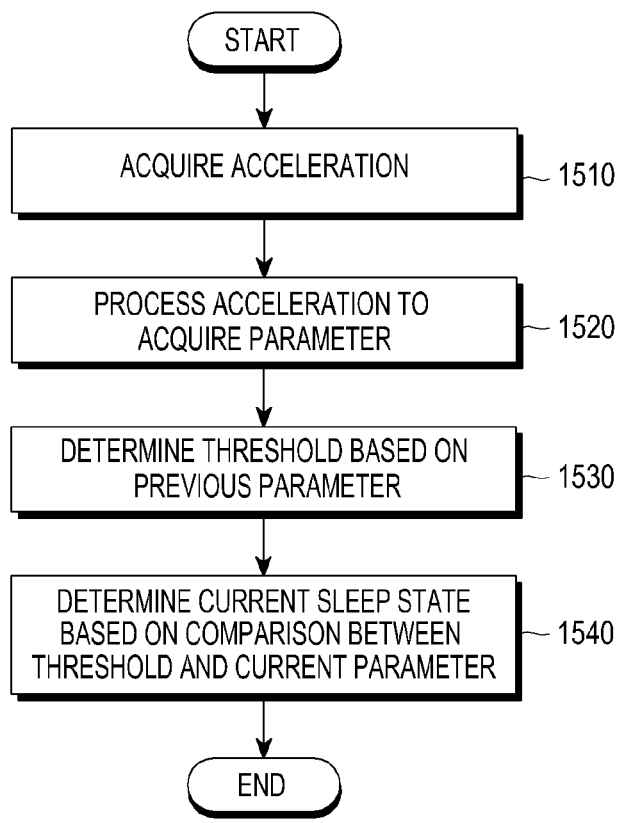
FIG. 15 is a flowchart illustrating a control method of the electronic device according to various embodiments of the present disclosure.

FIG. 15 is flowchart illustrating a control method of the electronic device according to various embodiments of the present disclosure.

In operation 1510, the electronic device 101 may measure the acceleration of the electronic device 101. The electronic device 101 may include, for example, a tri-axial accelerometer that is capable of measuring the acceleration of a user's wrist or arm through the tri-axial accelerometer. The electronic device 101 may further include a gyro sensor, a geomagnetic sensor, etc., as well as the tri-axial accelerometer, and measure the acceleration based on sensing signals from various sensors. Furthermore, the electronic device 101 may acquire a speed, a displacement, etc., as well as the acceleration, and determine an asleep state based on motion information including at least one of the acquired acceleration, speed, and displacement.

In operation 1520, the electronic device 101 may process the acquired acceleration to acquire a parameter. According to an embodiment, the electronic device 101 may calculate an average value of the acceleration and use the calculated average value as the parameter. A process of acquiring the parameter will be described below in more detail with respect to FIG. 16.

In operation 1530, the electronic device 101 may determine a threshold to be used for determining an asleep state of a current interval based on a previous parameter.

In operation 1540, the electronic device 101 may compare the determined threshold and the parameter of the current interval and determine the sleep state of the current interval based on a result of the comparison.

Figure 16:
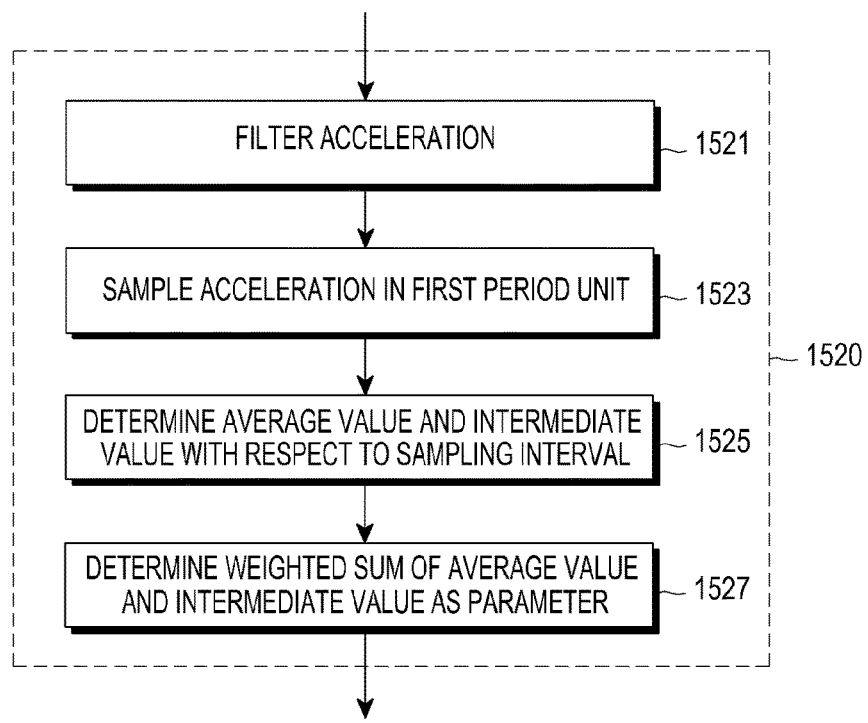
FIG. 16 is a flowchart illustrating a control method of the electronic device according to various embodiments of the present disclosure.

FIG. 16 is a flowchart illustrating a control method of the electronic device according to various embodiments of the present disclosure.

In operation 1521, the electronic device 101 may high-pass filter the acquired acceleration. According to an embodiment, the electronic device 101 may high-pass filter the acceleration with a cutoff frequency of 0.5 Hz.

In operation 1523, the electronic device 101 may sample the filtered acceleration in the first period unit. According to an embodiment, the electronic device 101 may sample the filtered acceleration in a unit of 30 seconds.

In operation 1525, the electronic device 101 may determine an average value and an intermediate value with respect to, for example, 10 sampling periods. In operation, 1527, the electronic device 101 may determine a weighted sum of the average value and the intermediate value. The number of sampling periods need not be 10, but may vary.

Figure 17A:
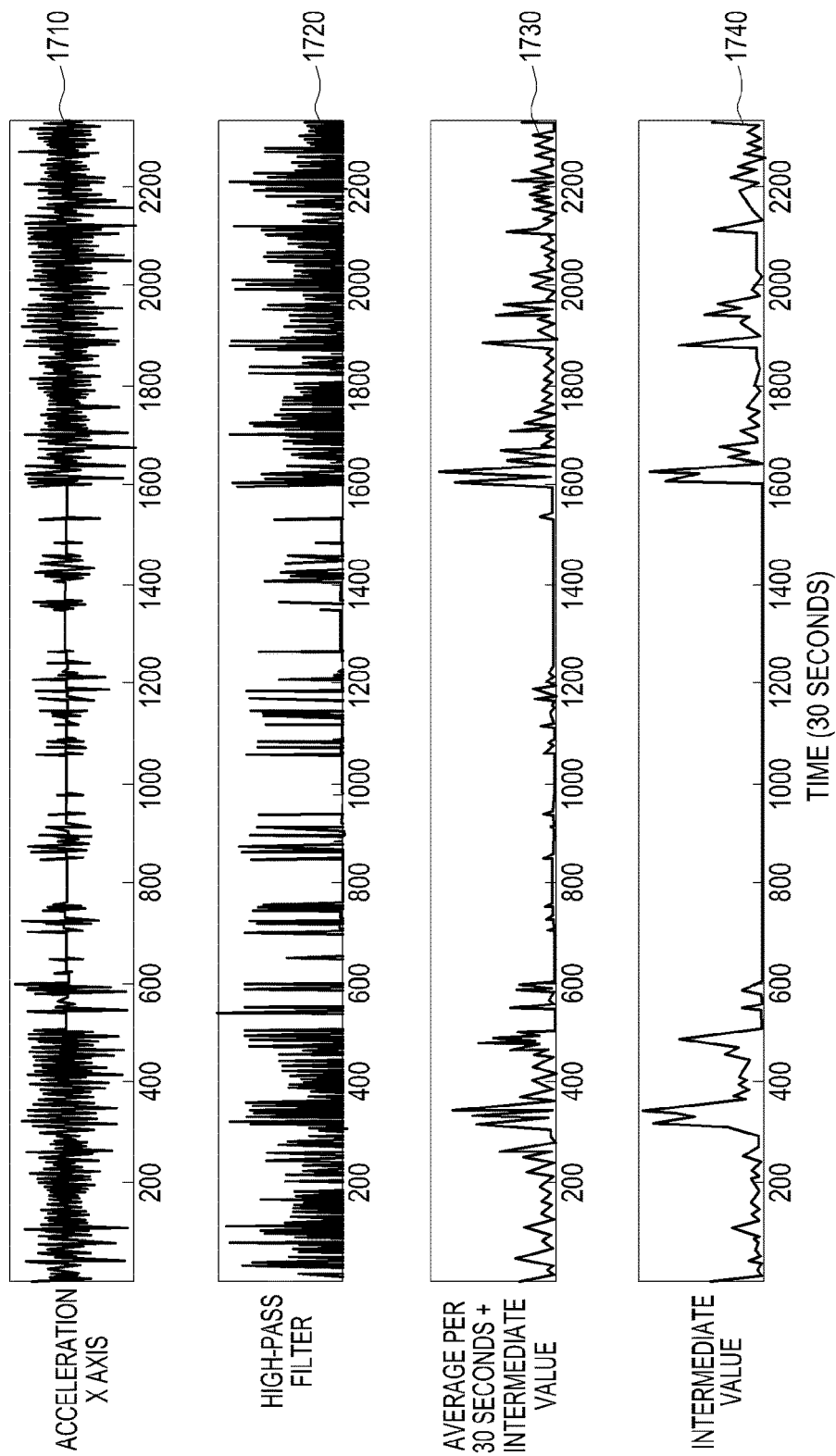
FIGS. 17A and 17B illustrate signals according to various embodiments of the present disclosure.
Figure 17B:
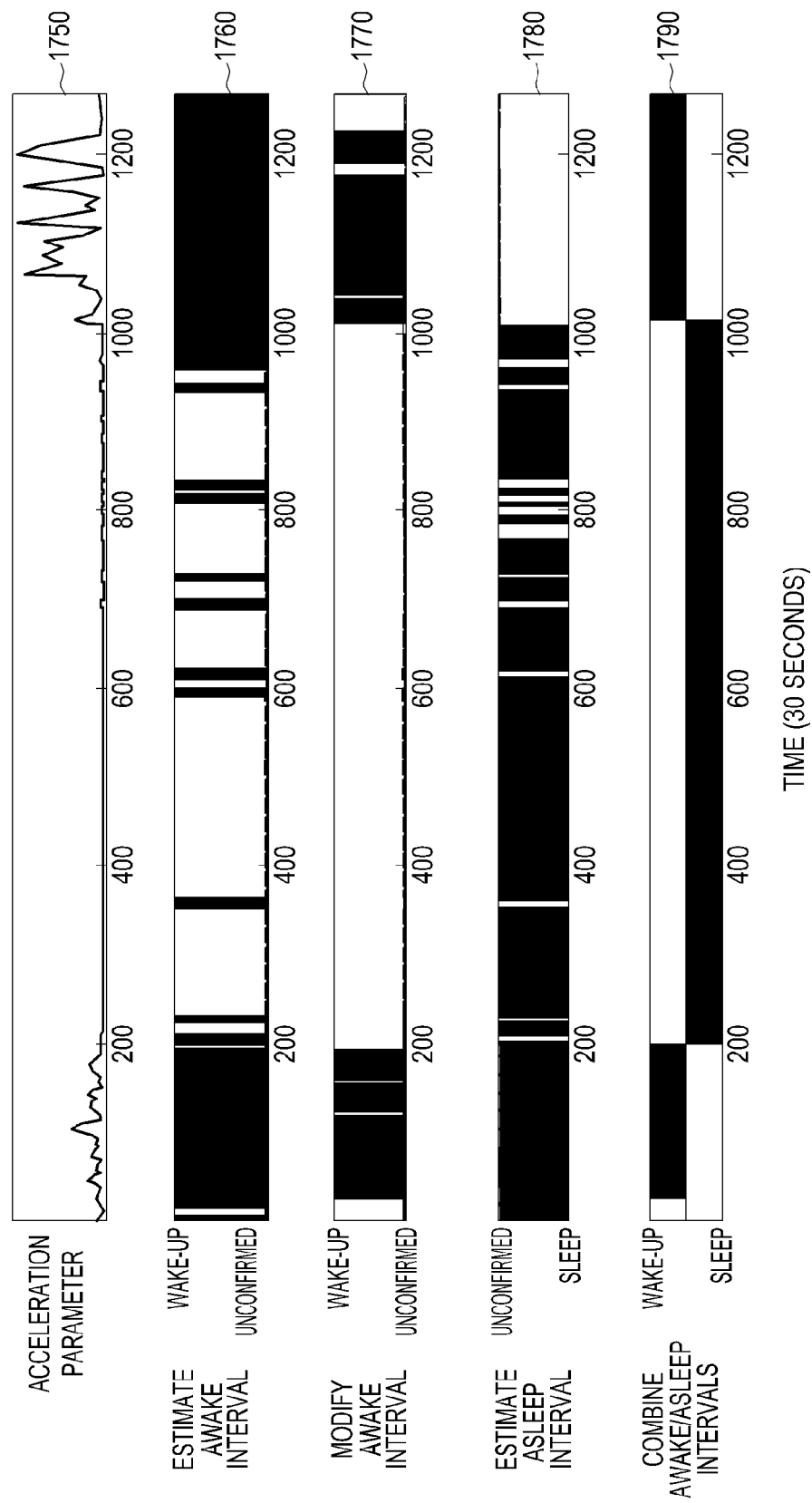

FIGS. 17A and 17B illustrate signals according to various embodiments of the present disclosure.

As illustrated in of FIG. 17A, the electronic device 101 may acquire acceleration data 1710. Although it is illustrated that the electronic device 101 acquires the acceleration data along an x axis, the electronic device 101 may acquire accelerations along at least one of x, y, and z axes. Furthermore, the electronic device 101 may use an absolute value of negative acceleration.

The electronic device 101 may high-pass filter the acceleration to acquire the filtered acceleration data 1720.

The electronic device 101 may determine a result of a sum of the average value and the intermediate value of the filtered acceleration data 1720 with respect to a preset period as the parameter 1730.

The electronic device 101 may determine a preset first interval before a current parameter. The electronic device 101 may calculate an average value of parameters of the first interval to determine a first threshold 1740, where the first interval is a time interval. As in FIG. 12D, the electronic device 101 may acquire a final parameter by performing a moving average on the acquired parameters in the unit of preset samples. The electronic device 101 may successively change the discretely averaged data and, accordingly, normalize the average of the parameters.

The electronic device 101 may determine an awake state 1760 based on the acceleration parameter 1750 and the current parameter. Furthermore, when a value generated by dividing a data sum of parameters of a predetermined previous interval by the number of pieces of data is equal to or smaller than a predetermined value, the electronic device 101 may change the interval into an unconfirmed period and acquire the changed awake state 1760.

The electronic device 101 may determine a preset second interval before a current parameter. The electronic device 101 may calculate an average value of parameters of the second interval to determine a second threshold. Furthermore, the electronic device 101 may determine an asleep state 1770 based on the second threshold and the current parameter.

The electronic device 101 may combine the awake state 1760 and the asleep state 1770 to determine sleep information 1790.

That is, as described above, the electronic device 101 may determine sleep information based on motion information as well as the galvanic skin response.

Figure 18:
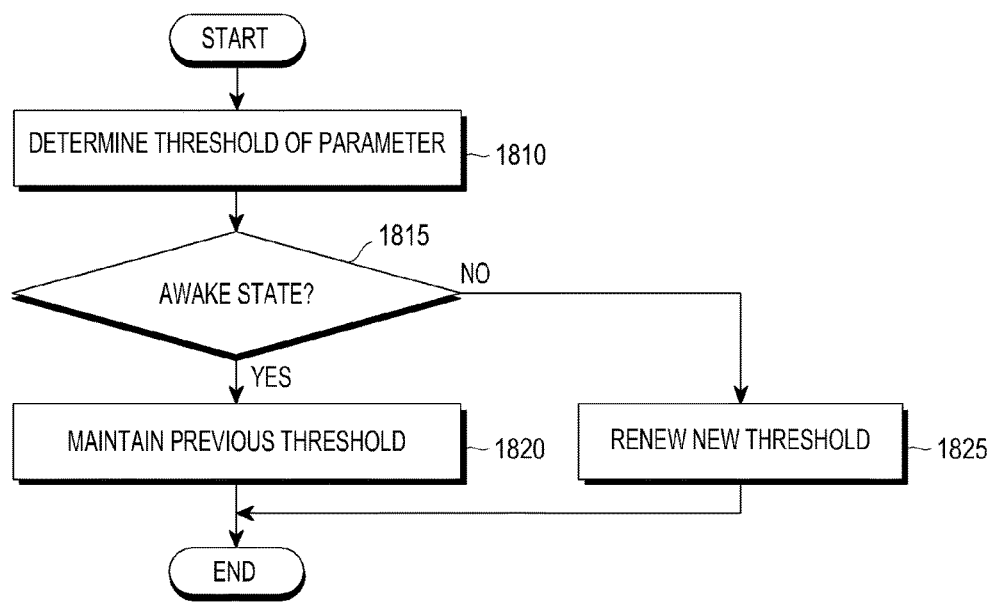
FIG. 18 is a flowchart illustrating a control method of the electronic device according to various embodiments of the present disclosure.

FIG. 18 is a flowchart illustrating a control method of the electronic device according to various embodiments of the present disclosure.

Referring to FIG. 18, in operation 1810, the electronic device 101 may determine a threshold of a parameter. The electronic device 101 may determine an asleep state determination threshold or an awake state determination threshold.

In operation 1815, the electronic device 101 may determine whether the current state is an awake state. According to an embodiment, when the parameter of the current state is larger than a multiple of the awake state determination threshold, the electronic device 101 may determine the current state as the awake state.

In operation 1820, when the current state is determined as the awake state, the electronic device 101 may maintain and use the threshold used in the current state when determining an awake state of a next current state.

In operation 1825, when the current state is determined as an unconfirmed state, the electronic device 101 may renew the threshold to a new threshold corresponding to a next current state when determining an awake state of the next current state.

When determining an asleep state, the electronic device 101 may review the threshold with respect to all cases where the current state is determined as the asleep state or the unconfirmed period.

Figure 19:
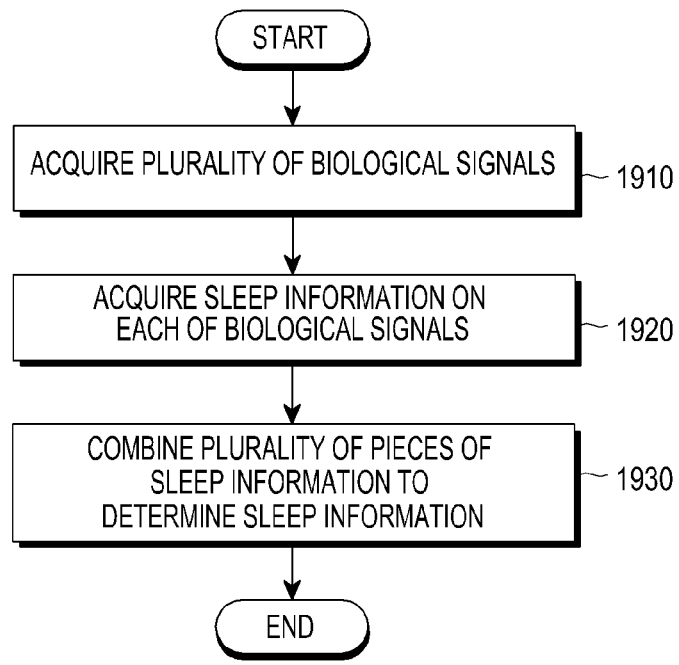
FIG. 19 is a flowchart illustrating a control method of the electronic device according to various embodiments of the present disclosure.

FIG. 19 is a flowchart illustrating a control method of the electronic device according to various embodiments of the present disclosure.

In operation 1910, the electronic device 101 may acquire a plurality of biological signals. According to an embodiment, the electronic device 101 may acquire, for example, galvanic skin response and motion information.

In operation 1920, the electronic device 101 may acquire sleep information for each of the plurality of biological signals. According to an embodiment, the electronic device 101 may acquire first sleep information based on the galvanic skin response and acquire second sleep information based on the motion information.

In operation 1930, the electronic device 101 may combine a plurality of pieces of sleep information to determine sleep information. According to an embodiment, the electronic device 101 may combine the first sleep information acquired based on the galvanic skin response and the second sleep information acquired based on the motion information. According to an embodiment, the electronic device 101 may change the first sleep information acquired based on the galvanic skin response into the second sleep information acquired based on the motion information. For example, the electronic device 101 may perform the change by reflecting the awake state acquired from the motion information in the first sleep information acquired based on the galvanic skin response.

Figure 20A:
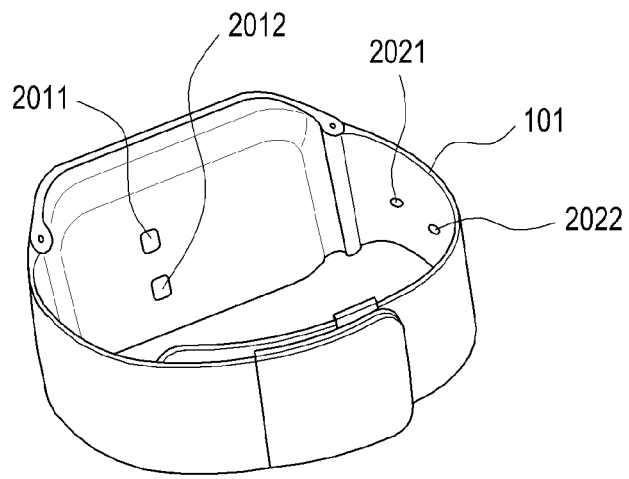
FIGS. 20A and 20B illustrate a concept of the electronic device according to various embodiments of the present disclosure.
Figure 20B:
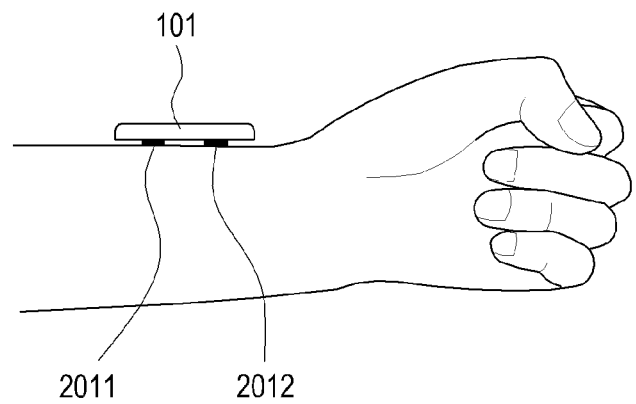

FIGS. 20A and 20B illustrate a concept of the electronic device according to various embodiments of the present disclosure.

As illustrated in FIG. 20A, the electronic device 101 may include one or more electrodes 2011, 2012, 2021, and 2022. For example, the electronic device 101 may control a pair of the electrodes 2011 and 2012 and a pair of the electrodes 2021 and 2022.

As illustrated in FIG. 20B, the electronic device 101 may apply potential to the electrode 2011 or allow current to pass through the electrode 2011, and measure at least one of potential, current, and impedance through the electrode 2012.

Figure 21:
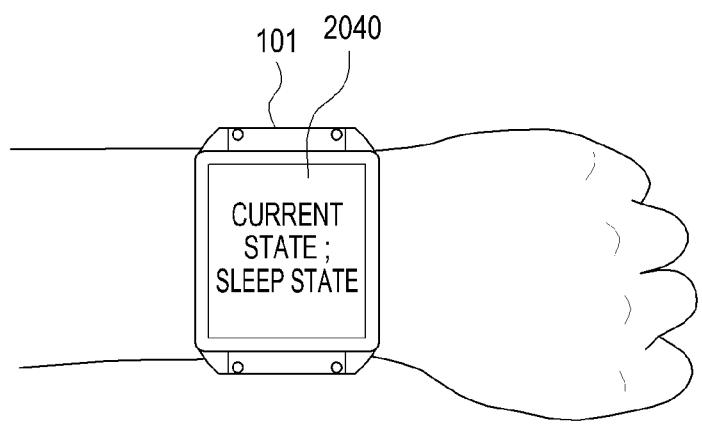
FIG. 21 illustrates a screen configuration of the electronic device according to various embodiments of the present disclosure.

FIG. 21 illustrates a screen configuration of the electronic device according to various embodiments of the present disclosure.

As illustrated in FIG. 21, the electronic device 101 may display a screen configuration 2040 indicating whether a current state is an asleep state or an awake state.

According to various embodiments of the present disclosure, a control method of an electronic device may include: acquiring a galvanic skin response; generating a first parameter for a first interval and a second parameter for a second interval based on the galvanic skin response, the second interval being an interval before the first interval; determining a first threshold corresponding to the first interval based on the second parameter; and determining an asleep state of the first interval based on the first threshold and the first parameter corresponding to the first interval. The first interval and the second interval may be time intervals.

According to various embodiments of the present disclosure, the control method may further include low-pass filtering the galvanic skin response. According to various embodiments of the present disclosure, the control method may further include sampling the galvanic skin response in the first period unit.

According to various embodiments of the present disclosure, the determining of the first parameter and the second parameter may include determining a first average value of sampled data of the first interval as the first parameter and determining a second average value of sampled data of the second interval as the second parameter. The first interval may be the first period unit and the second interval may be a preset multiple of the first period unit. The preset multiple may have different values in a case where an asleep state of the first interval is determined and a case where an awake state of the first interval is determined.

According to various embodiments of the present disclosure, the determining of the first threshold may include determining an average value of the second parameter of the second interval as the first threshold.

According to various embodiments of the present disclosure, the determining of the sleep state of the first interval may include, when the first parameter is smaller than a preset multiple of the first threshold or smaller than a preset constant, determining the first interval as the sleep state. The preset constant may be a preset asleep state constant According to various embodiments of the present disclosure, the determining of the asleep state of the first interval may include, when the first parameter is equal to or larger than a preset multiple of the first threshold or larger than or equal to a preset constant, determining the first interval as an unconfirmed interval. The preset constant may be a preset asleep state constant According to various embodiments of the present disclosure, the control method may further include determining an asleep state of the unconfirmed interval based on sleep states of intervals before and after the unconfirmed interval.

According to various embodiments of the present disclosure, the control method may further include renewing a threshold for determining an asleep state of a next interval.

According to various embodiments of the present disclosure, an electronic device may include: a sensor module that acquires a galvanic skin response; and a processor that generates a first parameter for a first interval and a second parameter for a second interval based on the galvanic skin response, determines a first threshold corresponding to the first interval based on the second parameter, and determines an asleep state of the first interval based on the first threshold and the first parameter corresponding to the first interval, wherein the second interval is an interval before the first interval.

According to various embodiments of the present disclosure, the electronic device may further include a filtering module that low-pass filters the galvanic skin response.

According to various embodiments of the present disclosure, the processor may sample the galvanic skin response in the first period unit.

According to various embodiments of the present disclosure, the processor may determine a first average value of sampled data of the first interval as the first parameter and determine a second average value of sampled data of the second interval as the second parameter. The first interval may be the first period unit and the second interval may be a preset multiple of the first period unit. The preset multiple may have different values in a case where an asleep state of the first interval is determined and a case where an awake state of the first interval is determined.

According to various embodiments of the present disclosure, the processor may determine an average value of the second parameter of the second interval as the first threshold.

According to various embodiments of the present disclosure, when the first parameter is smaller than a preset multiple of the first threshold or smaller than a preset constant, the processor may determine the first interval as the sleep state. The preset constant may be a preset asleep state constant.

According to various embodiments of the present disclosure, when the first parameter is equal to or larger than a preset multiple of the first threshold or larger than or equal to a preset constant, the processor may determine the first interval as an unconfirmed interval. The preset constant may be a preset asleep state constant.

According to various embodiments of the present disclosure, the processor may determine an asleep state of the unconfirmed interval based on sleep states of intervals before and after the unconfirmed interval.

According to various embodiments of the present disclosure, the processor may renew the first threshold to determine an asleep state of a next interval.

According to various embodiments of the present disclosure, a control method of an electronic device may include: acquiring a galvanic skin response; generating a first parameter for a first interval, a second parameter for a second interval, and a third parameter for a third interval based on the galvanic skin response, the second interval and the third interval being intervals before the first interval; determining an asleep state determination threshold corresponding to the first interval based on the second parameter and determining an awake state determination threshold corresponding to the first interval based on the third parameter; and determining an asleep state of the first interval based on the asleep state determination threshold and determining an awake state of the first interval based on the awake state determination threshold. A length of the second interval and a length of the third interval may be equal to each other or different from each other.

According to various embodiments of the present disclosure, the generating of the first parameter, the second parameter, and the third parameter may include sampling the first interval, the second interval, and the third interval in the first period unit and determining a first average value, a second average value, and a third average value of sampled data as the first parameter, the second parameter, and the third parameter, respectively.

According to various embodiments of the present disclosure, the determining of the asleep state determination threshold and the awake state determination threshold may include determining an average value of the second parameter of the second interval as the asleep state determination threshold and determining an average value of the third parameter of the third interval as the awake state determination threshold.

According to various embodiments of the present disclosure, the determining of the sleep state of the first interval based on the asleep state determination threshold and the determining of the awake state of the first interval based on the awake state determination threshold may include, when the first parameter is smaller than a preset multiple of the asleep state determination threshold or smaller than a preset constant, determining the first interval as the sleep state. The preset constant may be a preset awake state constant.

According to various embodiments of the present disclosure, the determining of the sleep state of the first interval based on the asleep state determination threshold and the determining of the awake state of the first interval based on the awake state determination threshold may include, when the first parameter is larger than or equal to a preset multiple of the asleep state determination threshold or larger than or equal to a preset constant, determining the first interval as an unconfirmed interval.

According to various embodiments of the present disclosure, the determining of the sleep state of the first interval based on the asleep state determination threshold and the determining of the awake state of the first interval based on the awake state determination threshold may include, when the first parameter is larger than a preset multiple of the awake state determination threshold or larger than a preset constant, determining the first interval as the awake state. The preset constant may be a preset awake state constant.

According to various embodiments of the present disclosure, the determining of the sleep state of the first interval based on the asleep state determination threshold and the determining of the awake state of the first interval based on the awake state determination threshold may include, when the first parameter is equal to or smaller than a preset multiple of the awake state determination threshold or equal to or smaller than a preset constant, determining the first interval as an unconfirmed interval. The preset constant may be a preset awake state constant.

According to various embodiments of the present disclosure, the control method may further include determining sleep information on the first interval based on the sleep state and the awake state of the first interval.

According to various embodiments of the present disclosure, the control method may further include maintaining a previously determined first threshold when the first interval is determined as the wake-state and renewing the first threshold to a new threshold when the first interval is determined as an unconfirmed interval.

According to various embodiments of the present disclosure, the control method may further include determining an asleep state of the unconfirmed interval based on sleep states of intervals before and after the unconfirmed interval.

According to various embodiments of the present disclosure, an electronic device may include: a sensor module that acquires a galvanic skin response; and a processor that generates a first parameter for a first interval, a second parameter for a second interval, and a third parameter for a third interval based on the galvanic skin response, determines an asleep state determination threshold corresponding to the first interval based on the second parameter, determines an awake state determination threshold corresponding to the first interval based on the third parameter, determines an asleep state of the first interval based on the asleep state determination threshold, and determines an awake state of the first interval based on the awake state determination threshold, wherein the second interval and the third interval are intervals before the first interval. The second interval and the third interval may be intervals before the first interval. A length of the second interval and a length of the third interval may be equal to each other or different from each other.

According to various embodiments of the present disclosure, the processor may sample the first interval, the second interval, and the third interval in the first period unit and determine a first average value, a second average value, and a third average value of sampled data as the first parameter, the second parameter, and the third parameter, respectively.

According to various embodiments of the present disclosure, the processor may determine an average value of the second parameter of the second interval as the asleep state determination threshold and determine an average value of the third parameter of the third interval as the awake state determination threshold.

According to various embodiments of the present disclosure, when the first parameter is smaller than a preset multiple of the asleep state determination threshold or smaller than a preset constant, the processor may determine the first interval as the sleep state. The preset constant may be a preset asleep state constant.

According to various embodiments of the present disclosure, when the first parameter is larger than or equal to a preset multiple of the asleep state determination threshold or larger than or equal to a preset constant, the processor may determine the first interval as an unconfirmed interval. The preset constant may be a preset asleep state constant.

According to various embodiments of the present disclosure, when the first parameter is larger than a preset multiple of the awake state determination threshold or larger than a preset constant, the processor may determine the first interval as the awake state. The preset constant may be a preset awake state constant.

According to various embodiments of the present disclosure, when the first parameter is equal to or smaller than a preset multiple of the awake state determination threshold or equal to or smaller than a preset constant, the processor may determine the first interval as an unconfirmed interval. The preset constant may be a preset awake state constant.

According to various embodiments of the present disclosure, the processor may determine sleep information on the first interval based on the sleep state and the awake state of the first interval.

According to various embodiments of the present disclosure, the processor may determine an asleep state of the unconfirmed interval based on sleep states of intervals before and after the unconfirmed interval.

According to various embodiments of the present disclosure, the processor may maintain a previously determined first threshold when the first interval is determined as the wake-state and renew the first threshold to a new threshold when the first interval is determined as an unconfirmed interval.

According to various embodiments of the present disclosure, a control method of an electronic device may include: acquiring motion information on the electronic device; generating a first parameter for a first interval and a second parameter for a second interval based on the motion information, the second interval being an interval before the first interval; determining a first threshold corresponding to the first interval based on the second parameter; and determining an asleep state of the first interval based on the first threshold and the first parameter corresponding to the first interval.

According to various embodiments of the present disclosure, an electronic device may include: a sensor module that acquires motion information on the electronic device; and a processor that generates a first parameter for a first interval and a second parameter for a second interval based on the motion information, determines a first threshold corresponding to the first interval based on the second parameter, and determines an asleep state of the first interval based on the first threshold and the first parameter corresponding to the first interval, wherein the second interval is an interval before the first interval.

According to various embodiments of the present disclosure, a control method of an electronic device may include: acquiring motion information on the electronic device; generating a first parameter for a first interval, a second parameter for a second interval, and a third parameter for a third interval based on the motion information, the second interval and the third interval being intervals before the first interval; determining an asleep state determination threshold corresponding to the first interval based on the second parameter and determining an awake state determination threshold corresponding to the first interval based on the third parameter; and determining an asleep state of the first interval based on the asleep state determination threshold and determining an awake state of the first interval based on the awake state determination threshold.

According to various embodiments of the present disclosure, an electronic device may include: a sensor module that acquires motion information on the electronic device; and a processor that generates a first parameter for a first interval, a second parameter for a second interval, and a third parameter for a third interval based on the motion information, determines an asleep state determination threshold corresponding to the first interval based on the second parameter, determines an awake state determination threshold corresponding to the first interval based on the third parameter, determines an asleep state of the first interval based on the asleep state determination threshold, and determines an awake state of the first interval based on the awake state determination threshold, wherein the second interval and the third interval are intervals before the first interval.

According to various embodiments of the present disclosure, a control method of an electronic device may include: acquiring at least one of a galvanic skin response and motion information on the electronic device; and determining and displaying one of an asleep state and an awake state corresponding to a current interval based on the acquired galvanic skin response.

According to various embodiments of the present disclosure, an electronic device may include: a sensor module that acquires at least one of a galvanic skin response and motion information on the electronic device; and a processor that determines and displays one of an asleep state and an awake state corresponding to a current interval based on the acquired galvanic skin response.

According to various embodiments of the present disclosure, a control method of an electronic device may include: acquiring at least one of a galvanic skin response and motion information on the electronic device; determining one of an asleep state and an awake state corresponding to a current interval based on the acquired galvanic skin response; determining one of an asleep state and an awake state corresponding to a current interval based on the motion information; and determining sleep information on the current interval based on the state of the current interval determined based on the galvanic skin response and the state of the current interval determined based on the motion information.

According to various embodiments of the present disclosure, an electronic device may include: a sensing module that acquires at least one of a galvanic skin response and motion information on the electronic device; and a processor that determines one of an asleep state and an awake state corresponding to a current interval based on the acquired galvanic skin response, determines one of an asleep state and an awake state corresponding to a current interval based on the motion information, and determines sleep information on the current interval based on the state of the current interval determined based on the galvanic skin response and the state of the current interval determined based on the motion information.

Figure 22:
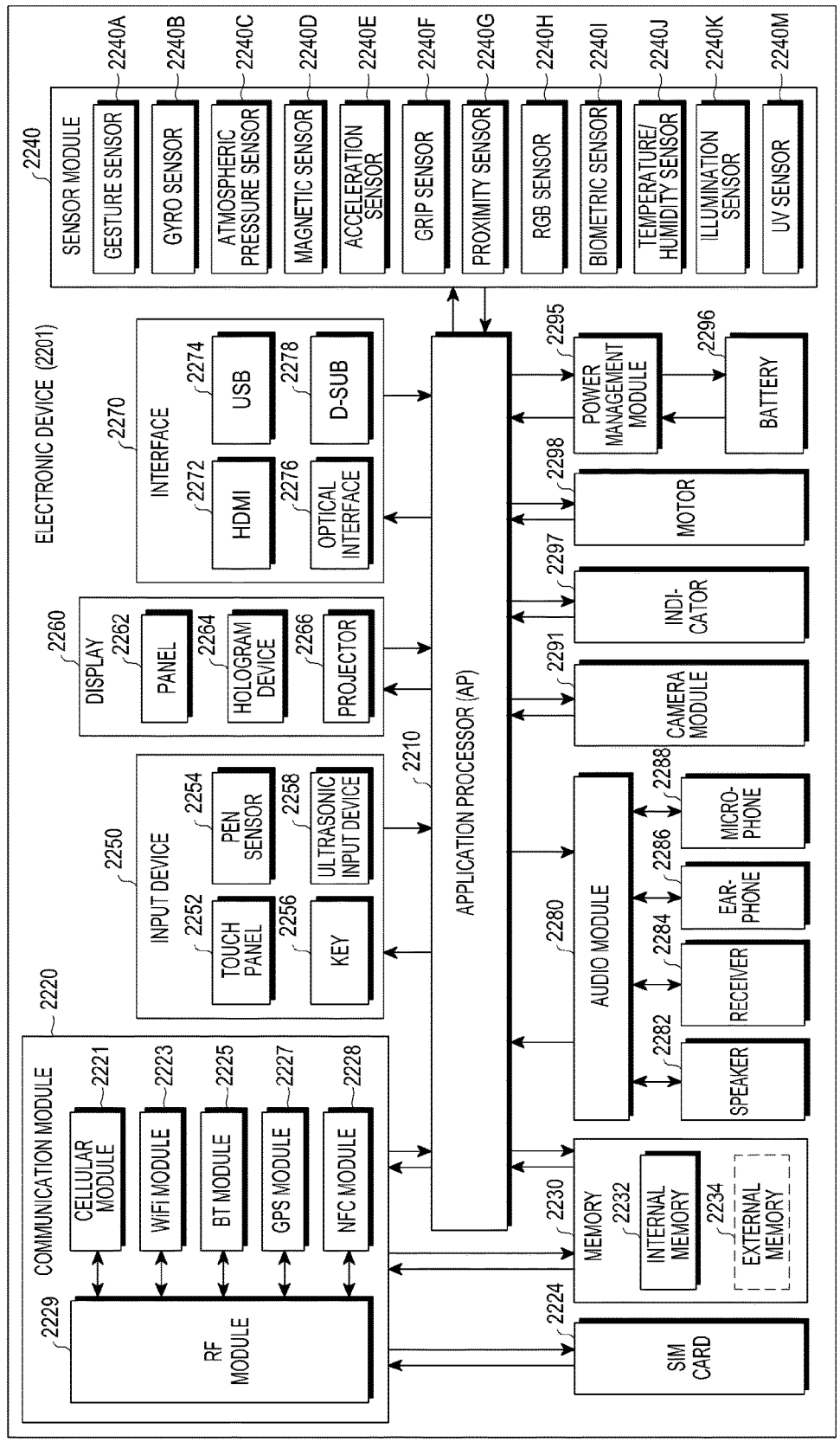
FIG. 22 is a block diagram of the electronic device according to various embodiments of the present disclosure.

FIG. 22 is a block diagram of an electronic device 2201 according to various embodiments of the present disclosure. The electronic device 2201 may include, for example, all or some of the electronic device 101 illustrated in FIG. 1, and vice-versa. The electronic device 2201 may include at least one Application Processor (AP) 2210, a communication module 2220, a Subscriber Identification Module (SIM) card 2224, a memory 2230, a sensor module 2240, an input device 2250, a display 2260, an interface 2270, an audio module 2280, a camera module 2291, a power management module 2295, a battery 2296, an indicator 2297, and a motor 2298.

The AP 2210 may control a plurality of hardware or software components connected thereto via an operating system or an application program and perform a variety of data processing and calculations. The AP 2210 may be implemented by, for example, a System on Chip (SoC). According to an embodiment, the AP 2210 may further include a Graphical Processing Unit (GPU) and/or an image signal processor. The AP 2210 may also include at least some (e.g., a cellular module 2221) of the components illustrated in FIG. 2. The AP 2210 may load commands or data received from at least one other component (e.g., a non-volatile memory), in a volatile memory, process the loaded commands or data, and store various types of data in a non-volatile memory.

The communication module 2220 may have a configuration equal or similar to the communication interface 170 of FIG. 1. The communication module 2220 may include, for example, a cellular module 2221, a Wi-Fi module 2223, a BT module 2225, a GPS module 2227, an NFC module 2228, and a Radio Frequency (RF) module 2229.

The cellular module 2221 may provide voice call, video call, text message services, or Internet services through, for example, a communication network. According to an embodiment, the cellular module 2221 may distinguish between and authenticate electronic devices 2201 within a communication network using a subscriber identification module (e.g., the SIM card 2224). According to an embodiment, the cellular module 2221 may perform at least some of the functions that may be provided by the AP 2210. According to an embodiment, the cellular module 2221 may include a Communication Processor (CP).

Each of the Wi-Fi module 2223, the BT module 2225, the GPS module 2227, and the NFC module 2228 may include, for example, a processor for processing data transmitted/received through the corresponding module. According to some embodiments, two or more of the cellular module 2221, the Wi-Fi module 2223, the BT module 2225, the GPS module 2227, and the NFC module 2228 may be included in one Integrated Chip (IC) or IC package.

The RF module 2229 may transmit/receive, for example, an RF signal. The RF module 2229 may include, for example, a transceiver, a Power Amp Module (PAM), a frequency filter, a Low Noise Amplifier (LNA) and/or an antenna. According to another embodiment, at least one of the cellular module 2221, the Wi-Fi module 2223, the BT module 2225, the GPS module 2227, and the NFC module 2228 may transmit/receive an RF signal through a separate RF module.

The SIM card 2224 may include a card including a subscriber identification module and/or an embedded SIM, and contain unique identification information (e.g., an Integrated Circuit Card Identifier (ICCID)) or subscriber information (e.g., an International Mobile Subscriber Identity (IMSI)).

The memory 2230 (e.g., the memory 130) may include an internal memory 2232 or an external memory 2234. The internal memory 2232 may include at least one of, for example, a volatile memory (e.g., a Dynamic Random Access Memory (DRAM), a Static RAM (SRAM), a Synchronous Dynamic RAM (SDRAM), etc.) and a non-volatile memory (e.g., a One Time Programmable Read Only Memory (OTPROM), a Programmable ROM (PROM), an Erasable and Programmable ROM (EPROM), an Electrically Erasable and Programmable ROM (EEPROM), a flash memory (e.g., a NAND flash memory or a NOR flash memory), a hard driver, or a Solid State Drive (SSD).

The external memory 2234 may further include a flash drive, for example, a Compact Flash (CF), a Secure Digital (SD), a Micro Secure Digital (Micro-SD), a Mini Secure Digital (Mini-SD), an extreme Digital (xD), a memory stick, etc. The external memory 2234 may be functionally and/or physically connected to the electronic device 2201 through various interfaces.

The sensor module 2240 may measure, for example, a physical quantity or detect an operation state of the electronic device 2201, and may convert the measured or detected information to an electrical signal. The sensor module 2240 may include at least one of, for example, a gesture sensor 2240A, a gyro sensor 2240B, an atmospheric pressure sensor 2240C, a magnetic sensor 2240D, an acceleration sensor 2240E, a grip sensor 2240F, a proximity sensor 2240G, a color sensor 2240H (e.g., a Red/Green/Blue (RGB) sensor), a biometric sensor 2240I, a temperature/humidity sensor 2240J, an illumination sensor 2240K, and an Ultra Violet (UV) sensor 2240M. Additionally or alternatively, the sensor module 2240 may include an E-nose sensor, an electromyography (EMG) sensor, an electroencephalogram (EEG) sensor, an electrocardiogram (ECG) sensor, an infrared (IR) sensor, an iris sensor, and/or a fingerprint sensor. The sensor module 2240 may further include a control circuit to control at least one sensor included therein. According to some embodiments, the electronic device 2201 may further include a processor configured to control the sensor module 2240 as a part of and/or separately from the AP 2210, and may control the sensor module 2240 while the AP 2210 is in an asleep state.

The input device 2250 may include, for example, a touch panel 2252, a (digital) pen sensor 2254, a key 2256, or an ultrasonic input device 2258. The touch panel 2252 may use at least one of, for example, a capacitive type, a resistive type, an infrared type, and an ultrasonic type. The touch panel 2252 may further include a control circuit. The touch panel 2252 may further include a tactile layer, and provide a tactile reaction to a user.

The (digital) pen sensor 2254 may include, for example, a recognition sheet which is a part of the touch panel or a separate recognition sheet. The key 2256 may include, for example, a physical button, an optical key or a keypad. The ultrasonic input device 2258 may input data through an input means that generates an ultrasonic signal, and the electronic device 2201 identify data by detecting a sound wave with a microphone (e.g., a microphone 2288).

The display 2260 (e.g., the display 160) may include a panel 2262, a hologram device 2264 or a projector 2266. The panel 2262 may include a component equal or similar to the display 160 of FIG. 1. The panel 2262 may be embodied to be, for example, flexible, transparent, or wearable. The panel 2262 may also be configured as a single module together with the touch panel 2252. The hologram device 2264 may show a stereoscopic image in the air by using interference of light. The projector 2266 may project light onto a screen to display an image. For example, the screen may be located inside or outside the electronic device 2201. According to an embodiment, the display 2260 may further include a control circuit for controlling the panel 2262, the hologram device 2264, or the projector 2266.

The interface 2270 may include, for example, a High-Definition Multimedia Interface (HDMI) 2272, a Universal Serial Bus (USB) 2274, an optical interface 2276, or a D-subminiature (D-sub) 2278. The interface 2270 may be included in, for example, the communication interface 170 illustrated in FIG. 1. Additionally or alternatively, the interface 2270 may include, for example, a Mobile High-definition Link (MHL) interface, a Secure Digital/Multi-Media Card (SD/MMC) interface, or an Infrared Data Association (IrDA) standard interface.

The audio module 2280 may convert a sound to an electrical signal and vice versa. At least some components of the audio module 2280 may be included in, for example, the I/O interface 150 illustrated in FIG. 1. The audio module 2280 may process sound information input or output through, for example, a speaker 2282, a receiver 2284, earphones 2286, the microphone 2288, etc.

The camera module 2291 corresponds to, for example, a device which may photograph a still image and a dynamic image. According to an embodiment, the camera module 2291 may include one or more image sensors (e.g., a front sensor or a back sensor), a lens, an Image Signal Processor (ISP) or a flash (e.g., LED or xenon lamp).

The power management module 2295 may manage, for example, power of the electronic device 2201. According to an embodiment, the power management module 2295 may include a Power Management Integrated Circuit (PMIC), a charger Integrated Circuit (IC), or a battery or fuel gauge. The PMIC may have a wired and/or wireless charging scheme. Examples of the wireless charging method may include, for example, a magnetic resonance method, a magnetic induction method, an electromagnetic method, etc. Additional circuits (e.g., a coil loop, a resonance circuit, a rectifier, etc.) for wireless charging may be further included. The battery gauge may measure, for example, the remaining amount of the battery 2296, a charging voltage and current, or temperature. The battery 2296 may include, for example, a rechargeable battery and/or a solar battery.

The indicator 2297 may indicate particular status of the electronic device 2201 or a part thereof (e.g., the AP 2210), for example, a booting status, a message status, a charging status, etc. The motor 2298 may convert an electrical signal into mechanical vibrations, and may generate a vibration or haptic effect. Although not illustrated, the electronic device 2201 may include a processing device (e.g., a GPU) for supporting mobile TV. The processing device for supporting mobile TV may process media data according to a standard of Digital Multimedia Broadcasting (DMB), Digital Video Broadcasting (DVB), media flow, etc.

Each of the components of the electronic device according to the present disclosure may be implemented by one or more components and the name of the corresponding component may vary depending on a type of the electronic device. In various embodiments, the electronic device may include at least one of the above-described elements. Some of the above-described elements may be omitted from the electronic device, or the electronic device may further include additional elements. Furthermore, some of the components of the electronic device according to the various embodiments of the present disclosure may be combined to form a single entity, and thus, may equivalently execute functions of the corresponding elements prior to the combination.

The term "module" as used herein may mean, for example, a unit including one of hardware, software, and firmware or a combination of two or more of them. The "module" may be interchangeably used with, for example, the term "unit," "logic," "logical block," "component," or "circuit." The "module" may be the smallest unit of an integrated component or a part thereof. The "module" may be the smallest unit that performs one or more functions or a part thereof. The "module" may be mechanically or electronically implemented. For example, the "module" according to the present disclosure may include at least one of an Application-Specific Integrated Circuit (ASIC) chip, a Field-Programmable Gate Arrays (FPGA), and a programmable-logic device for performing operations which has been known or are to be developed hereinafter.

According to various embodiments, at least some of the devices (e.g., modules or functions thereof) or the method (e.g., operations) according to the present disclosure may be implemented by a command stored in a computer-readable storage medium in a programming module form. A command may be executed by one or more processors (e.g., the processor 120) to carry out a function corresponding to the command. The computer-readable storage medium may be, for example, the memory 130.

The computer readable recoding medium may include a hard disk, a floppy disk, magnetic media (e.g., a magnetic tape), optical media (e.g., a Compact Disc Read Only Memory (CD-ROM) and a Digital Versatile Disc (DVD)), magneto-optical media (e.g., a floptical disk), a hardware device (e.g., a Read Only Memory (ROM), a Random Access Memory (RAM), a flash memory), etc. In addition, the program instructions may include high level language codes that can be executed in a computer by using an interpreter, as well as machine code from a compiler. The aforementioned hardware device may be configured to operate in part as one or more software modules in order to perform the operation of the present disclosure, and vice versa.

The programming module according to the present disclosure may include one or more of the aforementioned components or may further include other additional components, or some of the aforementioned components may be omitted. Operations executed by a module, a programming module, or other component elements according to various embodiments of the present disclosure may be executed sequentially, in parallel, repeatedly, or in a heuristic manner. Furthermore, some operations may be executed according to another order or may be omitted, or other operations may be added.

According to various embodiments of the present disclosure, a storage medium having commands stored therein is provided. The commands may be executed to allow one or more processors to perform one or more operations. The one or more operations may include: acquiring a galvanic skin response; generating a first parameter for a first interval and a second parameter for a second interval based on the galvanic skin response, the second interval being an interval before the first interval; determining a first threshold corresponding to the first interval based on the second parameter; and determining an asleep state of the first interval based on the first threshold and the first parameter corresponding to the first interval.

Various embodiments disclosed herein are provided merely to easily describe technical details of the present disclosure and to help the understanding of the present disclosure, and are not intended to limit the scope of the present disclosure. Therefore, it should be construed that all modifications and changes or modified and changed forms based on the technical idea of the present disclosure fall within the scope of the present disclosure.

What is claimed is:

1. A method for determining activity state, the method comprising:
    acquiring a galvanic skin response;
    generating, based on the galvanic skin response, a first parameter for a first interval and a second parameter for a second interval, wherein the first interval and the second interval are time intervals and the second interval is before the first interval;
    generating an asleep state determination threshold and awake state determination threshold based on the second parameter, wherein the asleep state determination threshold is smaller than the awake state determination threshold; and
    determining that an activity state in the first interval is asleep state in response to the first parameter being smaller than or equal to the asleep state determination threshold and determining that the activity state in the first interval is awake state in response to the first parameter being equal to or larger than the awake state determination threshold.

2. The method of claim 1, further comprising low-pass filtering the galvanic skin response.

3. The method of claim 2, further comprising sampling the galvanic skin response acquired for a first period unit, wherein the first period unit is equal to the first interval.

4. The method of claim 3, wherein generating the first parameter and the second parameter comprises calculating a first average value of sampled data for the first interval as the first parameter and calculating a second average value of sampled data of the second interval as the second parameter.

5. The method of claim 3, wherein the second interval corresponds to a preset multiple of the first period unit.

6. The method of claim 5, wherein the preset multiple has different values when the activity state being determined is an asleep state than when the activity state being determined is an awake state.

7. The method of claim 5, wherein generating the asleep state determination threshold comprises determining an average value of the second parameter of the second interval.

8. The method of claim 1, further comprising determining the activity state in the first interval is an unconfirmed state in response to the first parameter being larger than the asleep state determination threshold and smaller than the awake state determination threshold.

9. The method of claim 8, further comprising determining an activity state of the unconfirmed state based on at least one of the activity state of intervals before and after the first interval.

10. The method of claim 9, wherein the activity state of the unconfirmed interval is determined to be the asleep state when both of the intervals prior to and after the unconfirmed interval are in an asleep state.

11. An electronic device for determining activity state, the electronic device comprising:
a sensor module that acquires a galvanic skin response; and
a processor configured to:
generate a first parameter for a first interval and a second parameter for a second interval based on the galvanic skin response, wherein the first interval and the second interval are time intervals and the second interval is before the first interval,
determine an asleep state determination threshold and an awake state determination threshold based on the second parameter, wherein the asleep state determination threshold is smaller than the awake state determination threshold, and
determine that an activity state of the first interval is asleep state in response to the first parameter being smaller than or equal to the asleep state determination threshold and determine that the activity state in the first interval is awake state in response to the parameter being equal to or larger than the awake state determination threshold.

12. The electronic device of claim 11, further comprising a filtering module that low-pass filters the galvanic skin response.

13. The electronic device of claim 12, wherein the processor samples the galvanic skin response acquired for a first period unit, wherein the first period unit is equal to the first interval.

14. The electronic device of claim 13, wherein the processor generates the first parameter as a first average value of sampled data for the first interval and generates the second parameter as a second average value of sampled data of the second interval.

15. The electronic device of claim 13, wherein the second interval corresponds to a preset multiple of the first period unit.

16. The electronic device of claim 15, wherein the preset multiple has different values when the activity state being determined is an asleep state than when the activity state being determined is an awake state.

17. The electronic device of claim 15, wherein the processor generates the asleep state determination threshold as an average value of the second parameter of the second interval.

18. A method for determining activity state, the method comprising:
acquiring a galvanic skin response;
generating, based on the galvanic skin response, a first parameter for a first interval, a second parameter for a second interval, and a third parameter for a third interval, wherein the first interval, the second interval, and the third interval are time intervals, and the second interval and the third interval are before the first interval;
determining an asleep state determination threshold based on the second parameter and determining an awake state determination threshold based on the third parameter; and
determining that an activity state of the first interval is an asleep state in response to the first parameter being smaller than or equal to the asleep state determination threshold and determining that the activity state of the first interval is an awake state in response to the first parameter being equal to or larger than the awake state determination threshold.

* * * * *